(12) United States Patent
Sehgal

(10) Patent No.: US 8,877,060 B2
(45) Date of Patent: Nov. 4, 2014

(54) METHODS FOR REMOVING PATHOGENS FROM A PLATELET PREPARATION

(75) Inventor: Lakshman R. Sehgal, Dana Point, CA (US)

(73) Assignee: Biovec Transfusion, LLC, Chicago, IL (US)

(*) Notice: Subject to any disclaimer, the term of this patent is extended or adjusted under 35 U.S.C. 154(b) by 596 days.

(21) Appl. No.: 13/285,941

(22) Filed: Oct. 31, 2011

(65) Prior Publication Data

US 2012/0125847 A1    May 24, 2012

Related U.S. Application Data

(60) Provisional application No. 61/416,550, filed on Nov. 23, 2010.

(51) Int. Cl.
| | |
|---|---|
| *B01D 15/00* | (2006.01) |
| *C02F 1/44* | (2006.01) |
| *A61L 2/02* | (2006.01) |
| *A61M 1/02* | (2006.01) |
| *A61L 2/10* | (2006.01) |
| *A61L 2/08* | (2006.01) |

(52) U.S. Cl.
CPC ............. *A61M 1/0281* (2013.01); *A61L 2/10* (2013.01); *A61L 2/022* (2013.01); *A61L 2202/22* (2013.01); *A61L 2/088* (2013.01); *A61M 2202/0427* (2013.01); *B01D 2315/16* (2013.01)
USPC ............................ 210/639; 210/641; 210/646

(58) Field of Classification Search
CPC ..... A61L 2202/22; A61L 2/022; A61L 2/088; A61L 2/10; A61M 1/0281; A61M 2202/0427; B01D 2315/16
USPC .......................................... 210/639, 641, 646
See application file for complete search history.

(56) References Cited

U.S. PATENT DOCUMENTS

| | | |
|---|---|---|
| 5,242,810 A | 9/1993 | Maraganore et al. |
| 6,139,878 A | 10/2000 | Summaria et al. |
| 2005/0173315 A1 | 8/2005 | Bosch et al. |

OTHER PUBLICATIONS

Nagahara, T. et al., "Anticoagulant Factor Xa Inhibitor," Drugs of the Future, 20(6): 564-566, (1995).
Pruitt, J.R. et al., "Isoxazolines and Isoxazoles as Factor Xa Inhibitors," Bioorganic & Medicinal Chemistry Letters, 10: 685-689, (2000).
Quan, M.L et al. "Design and Synthesis of Isoxazoline Dervatves as Factor Xa Inhibtors. 1" J Med. Chem. 42: 2752-2759, (1999).
Sato, K et al., "Relatinship between the antithrombotic effect of YM-75466, a novel factor Xa inhibtor, and coagulation parameters in rats," European Journal of Pharmacology, 347: 231-236, (1998).

(Continued)

*Primary Examiner* — Dirk Bass
(74) *Attorney, Agent, or Firm* — Ping Wang; Andrews Kurth LLP

(57) ABSTRACT

The present application relates to a method for removing pathogens from a transfusion grade platelet composition. The method comprises the steps of passing a platelet preparation through a first tangential flow filtration (TFF) device having a TFF filter, and collecting a retentate from the TFF device, wherein the retentate comprises filtered platelets to be used for transfusion. The platelet preparation comprises a platelet activation inhibitor and an anti-coagulant. During the TFF process, a diafiltration solution is added to the retentate to maintain the volume of the platelets.

25 Claims, 6 Drawing Sheets
(5 of 6 Drawing Sheet(s) Filed in Color)

(56) References Cited

OTHER PUBLICATIONS

Wong, P.C. et al, "Nonpeptide Factor Xa Inhibitors: 1. Studies wth SF303 and SK549, a New Class of Potent Antithrombotics," Journal of Pharmacology and Experimental Therapeutics, 292(1):351-357, (2000).

Herbert, J. M. et al., "DX 9065A, a Novel, Synthetic, Selective and Orally Active Inhibitor of Factor Xa: In Vitro and in Vivo Studies," Journal of Pharmacology and Experimental Therapeutics, 276(3):1030-1038 (1996).

Nagahara, T. et al., "Design, Synthesis and Biological Activities of Orally Active Coagulation Factor Xa Inhibitors," Eur. J. Med. Chem. 30(suppl):140s-143s (1995).

Ewing, W.R. et al., "Progress in the design of inhibitors of coagulation factor Xa," Drugs of Future 24(7):771-787 (1999).

Baum, et al., Circulation. 98(17). Suppl 1: 179, (1998).

Ostrem, J.A. et al., "Characterization of an orally available and highly specific synthetic factor Xa Inhibitor," Thromb. Haemost. 73:1306 (1995).

Al-Obeidi, F et al., "Factor Xa Inhibitors," Expert Opinion on Therapeutic Patents 9(7):931-953 (1999).

Pinto, D.J.D., et al., "Discovery of 1-[3-(Aminomethyl)phenyl]-N-[3-fluoro-2'-(methylsulfonyl)-[1,1'-biphenyl]-4-yl]-3-(trifluoromethyl)-1H-pyrazole-5-carboxamide (DPC423), a Highly Potent, Selective, and Orally Bioavailable Inhibitor of Blood Coagulation Factor Xa," J. Med. Chem., 2001, 44 (4), pp. 566-578.

Hirsh and Weitz, Lancet, 93:203-241, (1999).

Fareed et al., Current Opinion in Cardiovascular, pulmonary and renal investigational drugs, 1:40-55, (1999).

Canellini, G., et al., "Bacterial Contamination of Platelet Concentrates: Perspectives for the Future", Lab Medicine, vol. 41 No. 5, pp. 301-305 (2010).

Grzenia D.L., et al., "Purification of Densonucleosis Virus by Tangential Flow Ultrafiltration", Biotechnol. Prog., vol. 22, No. 5, pp. 1346-1353 (2006).

Skripchenko, A., et al., "Thiazole orange, a DNA-binding photosensitizer with flexible structure, can inactivate pathogens in red blood cell suspensions while maintaining red cell storage properties", Transfusion, vol. 46, pp. 213-219 (2006).

The International Search Report and the Written Opinion of the International Searching Authority, mailed Jun. 26, 2012 (application No. PCT/US2011/058564, filed Oct. 31, 2011).

METHODS FOR REMOVING PATHOGENS FROM A PLATELET PREPARATION

This application claims priority from U.S. Provisional Application Ser. No. 61/416,550, filed on Nov. 23, 2010. The entirety of that provisional application is incorporated herein by reference.

FIELD

The present application relates generally to preservation of platelets and, in particular, to methods for removing pathogens from platelets prior to clinical application.

BACKGROUND

When blood vessels are damaged, cell fragments released from the bone marrow, called platelets, adhere to the walls of blood vessels and form clots to prevent blood loss. It is important to have adequate numbers of normally functioning platelets to maintain effective clotting, or coagulation, of the blood. Occasionally, when the body undergoes trauma, or when the platelets are unable to function properly, it is necessary to replace or transfer platelet components of blood into a patient. Most commonly, platelets are obtained from volunteer donors either as a component of a whole blood unit, or via plateletpheresis (withdrawing only platelets from a donor and re-infusing the remaining of the blood back into the donor). The platelets then are transferred to a patient as needed, a process referred to as "platelet transfusion".

The platelets, like other blood products of humans or animals, has a potential risk of being contaminated with pathogens such as viruses. Consequently, recipients of platelet transfusion must face the risk of being infected with high risk viruses such as the AIDS virus and various hepatitis viruses. Methods for preventing viral infection involved in the use of blood products have been developed. For example, a chemical deactivating method using a surfactant or methylene blue has been known as a method for deactivating viruses in blood products. However, any of these methods has problems such as denaturation of proteins, requirements for complicated procedures for removing used chemical substances, and remaining of chemical substances in the finished products. Accordingly, there still exist a need for methods that can effectively remove pathogens from stored platelets.

SUMMARY

One aspect of the present application relates to a method for removing pathogens from a platelet preparation prior to transfusion. The method comprises the steps of passing a platelet preparation through a first tangential flow filtration (TFF) device having a TFF filter with an average pore size in the range of 0.2 μm to 5 μm, and collecting a retentate from the TFF device, wherein the retentate comprises filtered platelets to be used for transfusion. The platelet preparation comprises a platelet activation inhibitor and an anti-coagulant. During the TFF process, a diafiltration solution is added to the retentate to maintain the volume of the platelets.

Another aspect of the present application relates to a method for preparing isolated platelets for storage. The method comprises the steps of passing isolated platelets through a tangential flow filtration (TFF) device having a TFF filter with an average pore size in the range of 0.2 μm to 5 μm, collecting a retentate from the TFF device, wherein the retentate comprises filtered platelets; adding a diafiltration solution to the retentate to maintain the volume of the platelets; and adding to the retentate an effective amount of a platelet activation inhibitor and an effective amount of an anti-coagulant.

Another aspect of the present application relates to a method for removing blood-borne virus from a platelet preparation prior to transfusion. The method comprises passing said platelet preparation through a tangential flow filtration (TFF) device having a TFF filter with an average pore size of 0.2 μm, the TFF filter has a retentate side and a permeate side; and collecting a retentate from the TFF device, wherein the retentate comprises filtered platelets to be used for transfusion, wherein a diafiltration solution is added to the retentate and wherein the platelet preparation comprises an platelet activation inhibitor and an anti-coagulant.

The present application provides an inexpensive and commercially feasible process for removing pathogens, such as viruses and bacteria, from blood components.

BRIEF DESCRIPTION OF FIGURES

The file of this patent contains at least one drawing executed in color. Copies of this patent with color drawings will be provided by the Patent and Trademark Office upon request and payment of the necessary fee.

DETAILED DESCRIPTION

Figure 1:
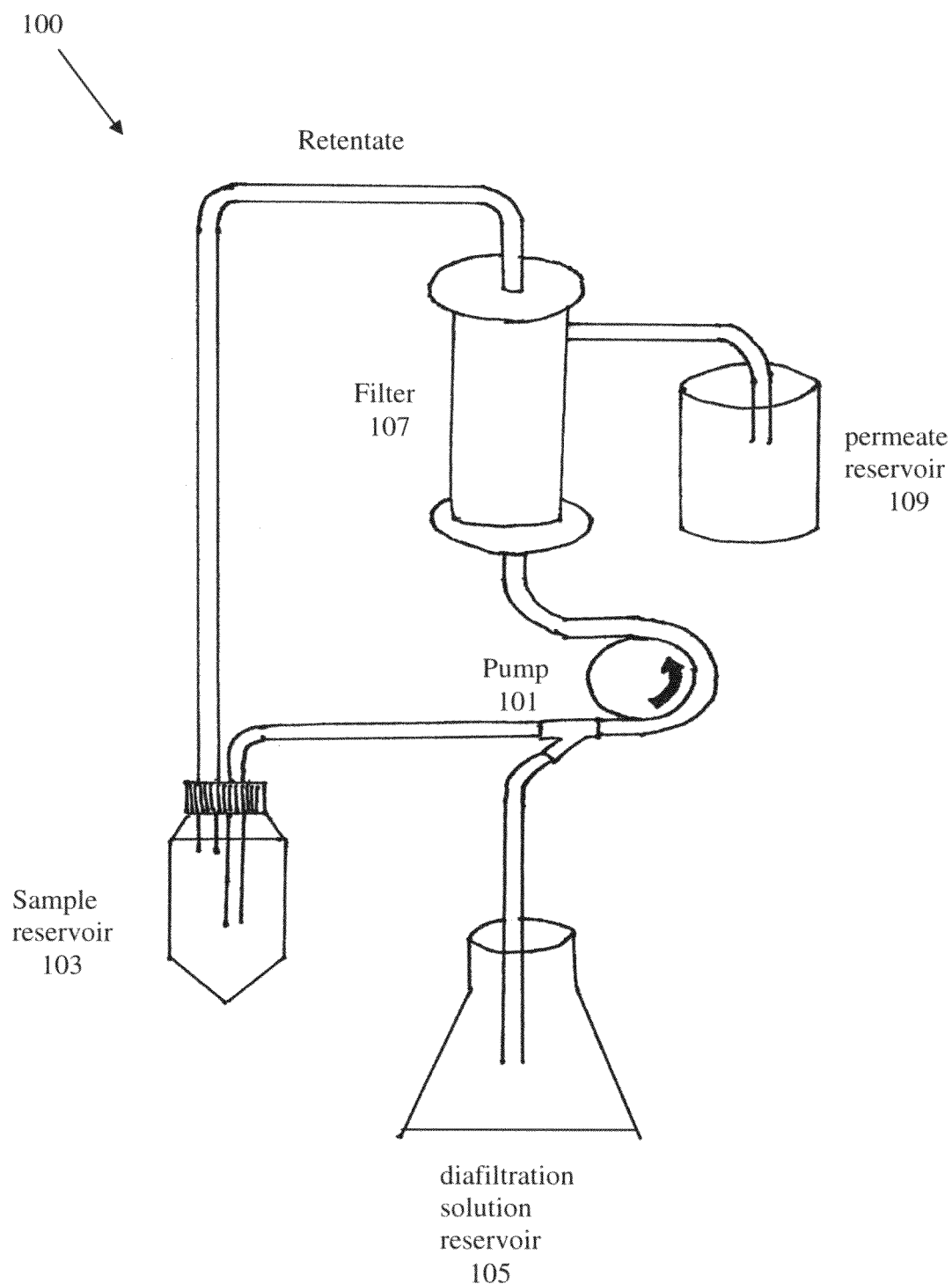
FIG. 1 is a diagram showing a continuous diafiltration system in accordance with the present application.

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention. Descriptions of specific applications are provided only as representative examples. Various modifications to the preferred embodiments will be readily apparent to one skilled in the art, and the general principles defined herein may be applied to other embodiments and applications without departing from the scope of the invention. The present invention is not intended to be limited to the embodiments shown, but is to be accorded the widest possible scope consistent with the principles and features disclosed herein.

One aspect of the present application relates to a method for removing pathogens from a platelet preparation by tangential flow filtration (TFF). The method comprises flowing the platelet preparation through a TFF filter to produce a retentate and a permeate and collecting the platelets in the retentate. The filter has an average pore size in the range of 0.2 micron to 5 micron. The platelet preparation comprises a platelet activation inhibitor and an anti-coagulant. Typically the retentate is combined with the platelet preparation and re-circulate through the TFF device for multiple passes through the TFF filter for a more complete removal of the pathogens.

The present application provides an inexpensive and commercially feasible process for removing pathogens, such as viruses and bacteria, from blood components. The TFF process further allows the removal of platelet activation inhibitor and anti-coagulants prior to the infusion of the platelet preparation.

As used hereinafter, the term "retentate" refers to the materials that flow by the surface of the filter in a TFF device but do not pass through the filter. When a fluid composition flow through a TFF device, particles with sizes larger than the average pore size of the TFF filter cannot pass through the filter and are likely to remain as the components of the retentate. As used hereinafter, the term "permeate" refers to the materials that pass through the filter in the TFF device. When a fluid composition flow through a TFF device, particles with sizes smaller than the average pore size of the TFF filter may pass through the filter and become components of the permeate.

In some embodiments, the method further comprises adding a diafiltration solution to the retentate so that the volume of the filtered platelet composition is maintained constant. For platelet preparations that is ready for clinical use, the TFF process also removes the preservation agents, such as the platelet activation inhibitors, anti-coagulants, oxygen carrier and photosensitizers in the filtered platelet preparation. In some embodiments, the method further comprises flowing an extraction fluid on the permeate side of the TFF filter in a counter flow direction relative to the flow of the platelet preparation. In yet other embodiments, the platelet preparation flows through two or more TFF filters that selectively remove different pathogens.

In certain embodiments, the platelet preparation further comprises a photosensitizer, which is activated by illumination prior to the TFF process to inactivate pathogens in the platelet preparation. In other embodiments, the photosensitizer is added to the filtered platelet composition and is then activated by illumination prior to the TFF process to inactivate pathogens in the platelet preparation.

The Platelet Preparation

The platelet preparation can be freshly prepared platelets or stored platelets. The platelets can be in the form of whole blood, a platelet-containing component of whole blood, or isolated platelets substantially free of red blood cells and other blood nutrients.

The platelets may be isolated from the whole blood using methods commonly used in the art. In one embodiment, a unit of whole blood is centrifuged using conditions sufficient to selectively precipitate cellular components of the blood (e.g., red blood cells and white blood cells). Under these conditions, the platelets remain suspended in the plasma. The platelet-rich plasma (PRP) may be removed from the precipitated blood cells, then centrifuged at a faster setting to harvest the platelets from the plasma.

In another embodiment, the whole blood is centrifuged so that the platelets become suspended in a "buffy coat" layer, which includes the platelets and white blood cells. The "buffy coat" is isolated and suspended in a small amount of red blood cells and plasma, then centrifuged again to separate the platelets and plasma from the red and white blood cells. Typically a unit of platelets obtained by the "buffy coat" method may contain about $3 \times 10^{11}$ platelets in approximately 300 milliliters plasma or other suitable preservative solution.

In another embodiment, apheresis platelets are collected using a mechanical device that draws blood from the donor and centrifuges the collected blood to separate out the platelets and other components to be collected. The remaining blood is returned to the donor. A unit of platelets collected by aphaeresis usually contains $5 \times 10^9$ platelets in 250 milliliters of plasma or other suitable fluid.

The platelet preparation may be supplemented with one or more agents selected from the group consisting of platelet activation inhibitors, anticoagulants, oxygen carriers, photosensitizers, or combinations thereof. These agents may be included to facilitate storage of the platelet composition prior to clinical application and may be subsequently removed prior to transfusion.

Thus, in addition to removing pathogens in one or more filtration stages, other agents exogenously added to the platelet preparation may be similarly removed by filtration prior to transfusion, including, but not limited to, platelet activation inhibitors, anticoagulants, photosensitizers and oxygen carriers.

Platelet Activation Inhibitors

Platelet activation inhibitors include any agent that reversibly impedes platelet activation and/or aggregation by blocking sites on the platelet surface can be used as the antiplatelet agent in the present invention. Platelet activation inhibitors include, but are not limited to, GPIIb/IIIa antagonists including bifunctional inhibitors of both GPIIb and IIIa, thrombin antagonists, P2Y12 receptor antagonists, and second messenger effectors.

In certain embodiments, the GPIIb/IIIa antagonists are GPIIb/IIIa antagonists that bind GPIIb/IIIa sites in a reversible manner. As used herein, the term "reversible" or "reversibly" refers to an act, such as binding or associating, that is capable of reverting back to an original condition prior to the act, for example the state of being unbound or disassociated, either with or without the assistance of an additional constituent. Examples of such GPIIb/IIIa antagonists include Eptifibatide (INTEGRILIN®, Schering-Plough Corporation, Kenilworth, N.J., U.S.A.), Orbofiban, Xemilofiban, Lamifiban, Tirofiban (AGGRASTAT®)), Abciximab (REOPRO®), Lefradafiban, Sibrafiban and Lotrafiban. In one embodiment, the GPIIb/IIIa antagonists are bifunctional inhibitors of both GPIIb/IIIa as described in U.S. Pat. No. 5,242,810, which is incorporated herein by reference.

In another embodiment, the platelet activation inhibitors include one or more thrombin antagonists. These agents interact with thrombin and block its catalytic activity on fibrinogen, platelets and other substrates. Examples of thrombin inhibitors include, but are not limited to, Lepirudin, Desirudin, Bivalirudin, Argatroban, Melagatran and Xirnelagatran.

In another embodiment, the platelet activation inhibitors include one or more P2Y12 receptor antagonists. Examples of P2Y12 receptor antagonists include, but are not limited to, prasugrel, cungrelor and AZD6140.

In another embodiment, the platelet activation inhibitors include one or more second messenger effectors. Second messenger effectors include any agent inhibiting a chemical pathway in a platelet so as to reduce platelet activation. Examples of second messenger effectors include, but are not limited to, "Thrombosol" (Life Cell Corp), linear or novel cyclic RGD peptide analogs, cyclic peptides, peptidomimetics, non-peptide analogs conjugated to nitric oxide donor, and the like, and mixtures thereof.

Second messenger effectors also include calcium sequestering agents, such as calcium channel blockers, α-blockers, β-adrenergic blockers and mixtures thereof. More specific examples of calcium sequestering agents include, but are not limited to, anticoagulant citrate dextrose solution, anticoagulant citrate dextrose solution modified, anticoagulant citrate phosphate dextrose solution, anticoagulant sodium citrate solution, anticoagulant citrate phosphate dextrose adenine solution, potassium oxalate, sodium citrate, sodium oxalate, amlodipine, bepridil hydrochloride, diltiazem hydrochloride, felodipine, isradipine, nicardipine hydrochloride, nifedipine, nimodipine, verapamil hydrochloride, doxazocin mesylate, phenoxybenzamine hydrochloride, phentolamine mesylate, prazosin hydrochloride, terazosin hydrochloride, tolazoline hydrochloride, acebutolol hydrochloride, atenolol, betaxolol hydrochloride, bisoprolol fumarate, carteolol hydrochloride, esmolol hydrochloride, indoramine hydrochloride, labetalol hydrochloride, levobunolol hydrochloride, metipranolol hydrochloride, metoprolol tartrate, nadolol, penbutolol sulfate, pindolol, propranolol hydrochloride, terazosin hydrochloride, timolol maleate, guanadrel sulfate, guanethidine monosul fate, metyrosine, reserpine and mixtures thereof.

In a preferred embodiment, the platelet activation inhibitor is a short-to-ultra short acting platelet activation inhibitor. By short-to-ultra-short-acting is meant that the platelet activation inhibitor has a circulating half life of 15 minutes to 8 hours, preferably 4 hours or less, after the infusion of the platelet activation inhibitor into the patient is stopped.

In one embodiment, the platelet activation inhibitor is an active agent that binds to or associates with the GPIIb/IIIa sites in a reversible manner and has a circulating half-life of inhibition of 4 hours or less. Short to ultra-short acting GPIIb/IIIa antagonist might include Eptifibatide (INTEGRILIN®), Tirofiban (AGGRASTAT®), Abciximab (REOPRO®), Lefradafiban, Sibrafiban, Orbofiban, Xemilofiban, Lotrafiban, XJ757, and XR299 (Class II).

In one embodiment, the preservation composition includes Eptifibatide. In another embodiment, the Eptifibatide is present in the composition at a final concentration of about 5-500 μg per unit of platelets. In another embodiment, the platelet activation inhibitor is Eptifibatide at a final concentration of about 50 μg per unit of platelets. Typically, a unit of platelets obtained by the buffy coat method contains about $3 \times 10^{11}$ platelets in approximately 300 ml of plasma or other suitable preservation composition. A unit of platelets collected by apheresis usually contain $5 \times 10^9$ platelets in 250 ml of plasma or other suitable fluid. In another embodiment, the platelet activation inhibitor is present in the composition at a final concentration that is 2-3 times of the therapeutic concentration. The term "therapeutic concentration" refers to the inhibitor concentration that is commonly used in the field for platelet preservation.

Anticoagulants

In another embodiment, the preservation composition further comprises one or more anticoagulants. Examples of anticoagulants include, but are not limited to, heparin, heparin substitutes, prothrombopenic anticoagulants, platelet phosphodiesterase inhibitors, dextrans, thrombin antagonists, and mixtures thereof.

Examples of heparin and heparin substitutes include, but are not limited to, heparin calcium, such as calciparin; heparin low-molecular weight, such as enoxaparin and lovenox; heparin sodium, such as heparin, lipo-hepin, Liquaemin sodium, and panheprin; and heparin sodium dihydroergotamine mesylate.

Suitable prothrombopenic anticoagulants are, for example, anisindione, dicumarol, warfarin sodium, and the like. More specific examples of phosphodiesterase inhibitors suitable for use in the invention include, but are not limited to, anagrelide, dipyridamole, pentoxifyllin, and theophylline. Examples of dextrans include, for example, dextran 70, such as HYSKON® (CooperSurgical, Inc., Shelton, Conn., U.S.A.) and MACRODEX® (Pharmalink, Inc., Upplands Vasby, Sweden), and dextran 75, such as GENTRAN® 75 (Baxter Healthcare Corporation, Deerfield, Ill., U.S.A.).

The anticoagulants may also include Xa inhibitors, IIa inhibitors, and mixtures thereof. Various direct Xa inhibitors were synthesized and advanced to clinical development (Phase I-II) for the prevention and treatment of venous thromboembolic disorders and certain settings of arterial thrombosis (Hirsh and Weitz, *Lancet,* 93:203-241, (1999); Nagahara et al., *Drugs of the Future,* 20: 564-566, (1995); Pinto et al., 44: 566-578, (2001); Pruitt et al., *Biorg. Med. Chem. Lett.,* 10: 685-689, (2000); Quan et al., *J. Med. Chem.* 42: 2752-2759, (1999); Sato et al., *Eur. J. Pharmacol.,* 347: 231-236, (1998); Wong et al, *J. Pharmacol. Exp. Therapy,* 292:351-357, (2000)). Direct IIa (thrombin) inhibitors include melagatran, the active form of pro-drug ximelagatran (Hirsh and Weitz, *Lancet,* 93:203-241, (1999); Fareed et al., *Current Opinion in Cardiovascular, pulmonary and renal investigational drugs,* 1:40-55, (1999)].

In certain embodiments, the anticoagulant is a short-to-ultra short acting anticoagulant. By short-to-ultra-short-acting is meant that the anticoagulant has a circulating half life of 15 minutes to 8 hours, preferably 4 hours or less, after the infusion of the platelet activation inhibitor into the patient is stopped. In one embodiment, the short-to-ultra short acting anticoagulant is a short-to-ultra short acting factor Xa inhibitor with a circulating half-life of less than 4 hours. Examples of ultra-short acting factor Xa inhibitors include, but are not limited to, DX-9065a, RPR-120844, BX-807834 and SEL series Xa inhibitors DX-9065a is a synthetic, non-peptide, propanoic acid derivative, 571 D selective factor Xa inhibitor (Dai chi). It directly inhibits factor Xa in a competitive manner with an inhibition constant in the nanomolar range (Herbert et al., *J. Pharmacol. Exp. Ther.* 276:1030-1038 (1996); Nagahara et al., *Eur. J. Med. Chem.* 30(suppl):140s-143s (1995)).

As a non-peptide, synthetic factor Xa inhibitor, RPR-120844 (Rhone-Poulenc Rorer), is one of a series of novel inhibitors which incorporate 3-(S)-amino-2-pyrrolidinone as a central template (Ewing et al., *Drugs of Future* 24(7):771-787 (1999)). This compound has a Ki of 7 nM with selectivity >150-fold over thrombin, activated protein C, plasmin and t-PA. It prolongs the PT and αPTT in a concentration-dependent manner, being more sensitive to the αPTT. It is a fast binding, reversible and competitive inhibitor of factor Xa.

BX-807834 has a molecular weight of 527 Da and a Ki of 110 μM for factor Xa as compared to 180 μM for TAP and 40 nM for DX-9065a (Baum et al., *Circulation.* 98 (17), Suppl 1: 179, (1998)).

The SEL series of novel factor Xa inhibitors (SEL-1915, SEL-2219, SEL-2489, SEL-2711: Selectide) are pentapeptides based on L-amino acids produced by combinatorial chemistry. They are highly selective for factor Xa and potency in the pM range. The Ki for SEL 2711, one of the most potent analogues, is 0.003 M for factor Xa and 40 M for thrombin (Ostrem et al., *Thromb. Haemost.* 73:1306 (1995); Al-Obeidi and Ostrem., *Exp. Opin. Ther. Patents* 9(7):931-953 (1999)).

In another embodiment, the short-to-ultra short acting anticoagulant is a short-to-ultra short acting factor IIa inhibitor. Examples of short-to-ultra short acting anticoagulant include, but are not limited to, DUP714, hirulog, hirudin, melgatran and combinations thereof. In another embodiment, the anticoagulant is present in the composition at a final concentration that is 2-3 times of the therapeutic concentration. The term "therapeutic concentration" refers to the anticoagulant concentration that is commonly used in the field for platelet preservation.

Oxygen Carrier

The oxygen carrier can be any suitable red blood cell substitute. In a preferred embodiment, the oxygen carrier is a hemoglobin-based oxygen carrier. Still more preferably, the oxygen carrier is an acellular hemoglobin-based oxygen carrier substantially free of red cell membrane (stroma) contaminants.

The use of a hemoglobin-based oxygen carrier, even in small volumes, can provide significantly greater concentration of oxygen than amounts currently made available using oxygen-permeable storage bags. Adding oxygen carrier(s) (e.g., a stroma-free hemoglobin solution) to platelets can allow for the use of gas impermeable bags, which can reduce the high cost associated with using gas permeable bags.

The term "pharmaceutically acceptable oxygen carrier" as used herein refers to a substance that has passed the FDA human safety trials at a hemoglobin dosage of 0.5 g/kg body weight or higher. An oxygen carrier suitable for the invention can be hemoglobin, ferroprotoporphyrin, perfluorochemicals (PFCs), and the like. The hemoglobin can be from human or any other suitable mammalian source. In a preferred embodiment, the oxygen carriers are added to the processed platelet composition resulting in a hemoglobin concentration between 1 to 18 gm/dl and a methemoglobin concentration of less than about 5%. The hemoglobin based oxygen carrier can be chemically modified to mimic the oxygen loading and unloading characteristics of fresh red blood cells. Additionally, the chemical modification can enhance the buffering capacity of the preferred embodiment and preserve normal physiologic pH.

In some embodiments, one or more anti-microbial agents may be added to the platelet composition before or after any of the filtration steps described herein. Preferably, the anti-microbial agent is a short-to-ultra-short acting broad spectrum anti-microbial agent. By short-to-ultra-short-acting is meant that the anti-microbial agent has a circulating half life of 15 minutes to 8 hours, preferably 4 hours or less, after the infusion of the platelet activation inhibitor into the patient is stopped. Examples of such agents include, but are not limited to, penicillin, monobactam, cephalosporin, carbapenems, vancomycin, isoniazid (INH), ethambutol, aminoglycoside, tetracycline, chloramphenicol, macrolide, rifamycin, quinolone, fluoroquinolone, sulfonamide, polyene antibiotic, triazole, griseofulvin, and derivatives and combinations thereof.

In another embodiment, antibodies may be selectively removed prior to any of the filtration steps or in conjunction with any of the filtration steps. Antibodies may be selectively removed from the platelet composition by affinity chromatography using various affinity matrices specific for one or more immunoglobulin classes, including IgG, IgA, IgE, IgM, IgY antibodies. Exemplary affinity matrices include protein A-Sepharose and protein G-Sepharose beads for binding total IgG; protein L-agarose for binding IgG, IgM, IgA, IgE, and IgD (Actigen AS, Oslo, Norway); and Kaptiv-GY™ (IgG, IgY), Kaptiv-AE™ (IgA, IgE), and Kaptiv-M™ (IgM) affinity matrices (Tecnogen S.p.A., Piana di Monte Verna, Italy). Platelet compositions may be passed through one or more of the above described affinity matrices to immunodeplete antibodies therefrom using procedures well known to those of skill in the art. When used in conjunction with diafiltration, it is possible to ensure complete removal of all antibodies (>6 logs) from a platelet composition. It is believed that such removal greatly reduces the risk of acquiring transfusion related acute lung injury through transfusions.

Additionally, the platelet composition may be sterilized by chemical, radiation, or a combination thereof. For example, the platelet composition can be sterilized by chemical filtration; ultraviolet radiation, such as UVA, UVB, and UVC or monochromatic UV radiation at 254 nm, for example; gamma-radiation; ionizing radiation, such as x-ray radiation; or by using a chemical as a photosensitizer as further described herein.

Photosensitizer

In another embodiment, one or more photosensitizers are added to the platelet composition to form a mixture which is illuminated with light under conditions sufficient to activate the photosensitizer and inactivate one or more pathogens in the mixture. The term "photosensitizer" as used herein refers to a compound which absorbs radiation at one or more defined wavelengths and has the ability to utilize the absorbed energy to carry out a chemical process, such as facilitating the formation of phototoxic species sufficient for killing one or more pathogens.

Exemplary photosensitizers, include, but are not limited to, quinolines, quinolones, riboflavin, nitric oxide, pyrrole derived macrocyclic compounds, naturally occurring or synthetic porphyrins and derivatives thereof naturally occurring or synthetic chlorins and derivatives thereof, naturally occurring or synthetic bacteriochlorins and derivatives thereof, naturally occurring or synthetic isobacteriochlorins and derivatives thereof, naturally occurring or synthetic phthalocyanines and derivatives thereof, naturally occurring or synthetic naphthalocyanines and derivatives thereof, naturally occurring or synthetic porphycenes and derivatives thereof, naturally occurring or synthetic porphycyanines and derivatives thereof, naturally occurring or synthetic pentaphyrins and derivatives thereof, naturally occurring or synthetic sapphyrins and derivatives thereof, naturally occurring or synthetic benzochlorins and derivatives thereof, naturally occurring or synthetic chlorophylls and derivatives thereof, naturally occurring or synthetic azaporphyrins and derivatives thereof, the metabolic porphyrinic precursor 5-amino levulinic acid and any naturally occurring or synthetic derivatives thereof, PHOTOFRIN™, synthetic diporphyrins and dichlorins, O-substituted tetraphenyl porphyrins (picket fence porphyrins), 3,1-meso tetrakis (o-propionamido phenyl) porphyrin, verdins, purpurins (e.g., tin and zinc derivatives of octaethylpurpurin (NT2), and etiopurpurin (ET2)), zinc naphthalocyanines, anthracenediones, anthrapyrazoles, aminoanthraquinone, phenoxazine dyes, chlorins (e.g., chlorin e6, and mono-1-aspartyl derivative of chlorin e6), benzoporphyrin derivatives (BPD) (e.g., benzoporphyrin monoacid derivatives, tetracyanoethylene adducts of benzoporphyrin, dimethyl acetylenedicarboxylate adducts of benzoporphyrin, Diels-Adler adducts, and monoacid ring "a"

derivative of benzoporphyrin), low density lipoprotein mediated localization parameters similar to those observed with hematoporphyrin derivative (HPD), sulfonated aluminum phthalocyanine (Pc) (sulfonated AlPc, disulfonated (AlPcS$_2$), tetrasulfonated derivative, sulfonated aluminum naphthalocyanines, chloroaluminum sulfonated phthalocyanine (CASP)), phenothiazine derivatives, chalcogenapyrylium dyes cationic selena and tellurapyrylium derivatives, ring-substituted cationic PC, pheophorbide alpha, hydroporphyrins (e.g., chlorins and bacteriochlorins of the tetra(hydroxyphenyl) porphyrin series), phthalocyanines, hematoporphyrin (BP), protoporphyrin, uroporphyrin III, coproporphyrin III, protoporphyrin IX, 5-amino levulinic acid, pyrro ethane boron difluorides, indocyanine green, zinc phthalocyanine, dihematoporphyrin (514 nm), benzoporphyrin derivatives, carotenoporphyrins, hematoporphyrin and porphyrin derivatives, rose bengal (550 nm), bacteriochlorin A (760 nm), epigallocatechin, epicatechin derivatives, hypocrellin B, urocanic acid, indoleacrylic acid, rhodium complexes, etiobenzochlorins, octaethylbenzochlorins, sulfonated Pc-naphthalocyanine, silicon naphthalocyanines, chloroaluminum sulfonated phthalocyanine (610 nm), phthalocyanine derivatives, iminium salt benzochlorins and other iminium salt complexes, Merocyanin 540, Hoechst 33258, and other DNA-binding fluorochromes, psoralens, acridine compounds, suprofen, tiaprofenic acid, non-steroidal anti-inflammatory drugs, methylpheophorbide-a-(hexyl-ether) and other pheophorbides, furocou arin hydroperoxides, Victoria blue BO, methylene blue, toluidine blue, porphycene compounds, indocyanines, psoralens, coumarins or other polycyclic ring compounds, free radical and reactive forms of oxygen, phenothiazin-5-ium dyes and combinations of the above.

In one embodiment, the photosensitizer is sensitive to (or absorbs) ultraviolet (UV) light. In another embodiment, the photosensitizer is sensitive to (or absorbs) non-UV light, including longer wavelengths ranging from about 600 to about 1200 nm. In a related embodiment, a combination of photosensitizers may be utilized, wherein at least one is sensitive to UV light and one is sensitive to non-UV light.

In another embodiment, the photosensitizer is a compound preferentially adsorbing to nucleic acids, such as psoralen, thereby focusing its photodynamic effects upon pathogens or cells with replicating nucleic acids with little or no effect upon accompanying platelets and other non-nucleated cells or proteins.

The photosensitizer may be an endogenous photosensitizer or a non-endogenous photosensitizer. The term "endogenous" as used herein refers to photosensitizers naturally found in a human or mammalian body, either as a result of synthesis by the body, ingestion (e.g. vitamins), or formation of metabolites and/or byproducts in vivo. Exemplary endogenous photosensitizers, include, but are not limited to, alloxazines, such as 7,8-dimethyl-10-ribityl isoalloxazine (riboflavin or vitamin B2), 7,8,10-trimethylisoalloxazine (lumiflavin), 7,8-dimethylalloxazine (lumichrome), isoalloxazine-adenine dinucleotide (flavine adenine dinucleotide (FAD)), alloxazine mononucleotide (also known as flavine mononucleotide (FMN) and riboflavine-5-phosphate), vitamin Ks, including vitamin K1, vitamin K1 oxide, vitamin vitamin K5, vitamin K-S (II), vitamin K6, vitamin K7, vitamin L, their metabolites and precursors, and napththoquinones, naphthalenes, naphthols and their derivatives having planar molecular conformations. The term "alloxazine" includes isoalloxazines. Endogenously-based derivative photosensitizers include synthetically derived analogs and homologs of endogenous photosensitizers which may have or lack lower (1-5) alkyl or halogen substituents of the photosensitizers from which they are derived, and which preserve the function and substantial non-toxicity thereof.

When endogenous photosensitizers are used, particularly when such photosensitizers are not inherently toxic or do not yield toxic photoproducts after photoradiation, it may be unnecessary to remove the photosensitizer prior to transfusion of the treated platelets. When using photosensitizers that are toxic or yield toxic photoproducts, however, the toxic products may be removed by diafiltration or other suitable removal means, including those as further described below.

In preferred embodiments, the photosensitizer is riboflavin or psoralen. In yet another embodiment, the photosensitizer is methylene blue.

The photosensitizer is added in an amount sufficient for inactivating one or more blood-borne pathogens, preferably all blood-borne pathogens, but less than a toxic (to humans or other mammals) or insoluble amount. Preferably, the photosensitizer is used in a concentration of at least about 1 µM up to the solubility of the photosensitizer in the fluid medium. There is a reciprocal relationship between photosensitizer compositions and light dose, thus, determination of effective concentration, suitable wavelength, light intensity, and duration of illumination is within ordinary skill in the art.

Quenchers may also be added to the platelet composition or diafiltration solution to make the irradiation process more efficient and selective. Such quenchers include antioxidants or other agents to prevent damage to desired fluid components or to improve the rate of pathogen inactivation and are exemplified by adenine, histidine, cysteine, tyrosine, tryptophan, ascorbate, N-acetyl-L-cysteine, propyl gallate, glutathione, mercaptopropionylglycine, dithiothreotol, nicotinamide, BHT, BHA, lysine, serine, methionine, glucose, mannitol, vitamin E, trolox, alpha-tocopheral acetate and various derivatives, glycerol, and mixtures thereof. Quenchers are added in an amount necessary to prevent damage to the platelets.

When subjecting platelets to UV light, the platelets may build up lactic acid levels through the glycolytic pathway causing a drop in the pH of the solution and/or decreased cell quality during storage. One way to reduce these problems is to add an agent blocking or reducing energy production through the glycolytic pathway. Accordingly, 2-deoxy-D-glucose may be added to the diafiltration solution at a concentration of 1 mM to 10 mM, either before UV treatment, after UV treatment, or both.

The TFF Filter

The filter can be any filter suitable for tangential flow filtration (TFT) and can include one or more filter membranes as further described herein. In one embodiment, the filter comprises a hollow fiber module comprising a bundle of filter membranes, each filter membrane being shaped in the form of a hollow tube. In this case, the feed stream is pumped into the lumen of the tubes such that permeate passes through the membrane to the shell side, where it is removed. Typically, the hollow tube comprises a diameter between about 0.1 to about 2.0 mm. In one embodiment, the filter membrane has an inner diameter of at least 0.5 mm.

In another embodiment, the filter comprises a flat plate (or cassette or capsule) module comprising layers of membrane, with or without alternating layers of separator screen, stacked together and sealed in a package. Feed fluid is pumped into alternating channels at one end of the stack and the permeate passes through the membrane into the permeate channels.

In yet another embodiment, the filter comprises a spiral wound module comprising alternating layers of membrane and separator screen wound around a hollow central core. In this case, the feed stream is pumped into one end and flows down the axis of the cartridge, whereby permeate passes through the membrane and spirals to the core, where it is removed.

The filter membrane has a pore size that is large enough to allow plasma, including plasma components and other agents for removal (e.g., antiplatelet agents or anticoagulants) to pass through and small enough to retain platelets.

In one embodiment the diafiltration membrane is selected to have a pore size rated 2-5× smaller than anything to be retained. In another embodiment, the membrane is selected to have a pore size rate 2-5× larger than anything to be passed through the membrane.

Blood components in a platelet composition may vary widely in size within a species and between two or more species. Human platelets are typically between 2 μm to 4 μm in diameter, more typically between 2.6 μm to 2.9 μm. Human red blood cells are typically between 6 μm to 8 μm in diameter. Human white blood cells include, for example, granulocytes, lymphocytes, and monocytes. Human granulocytes further include neutrophils (10-12 μm), eosinophils (10-12 μm), and basophils (12-15 μm). Human lymphocytes are typically between 7-8 μm in diameter. Human monocytes are typically 14-17 μm in diameter, whereas macrophages are typically about 21 μm in diameter. By contrast, other plasma components, such as human IgG (150 kD) and human IgM (900 kD) are less than 0.1 μm in size, and human serum albumin (67 kD) is less than 0.01 μm in size. All known viruses are 0.1 micron or smaller. The sizes of bacteria vary. For example, the size of *Staphylococcus* is 0.5-1.0 micron. The size of the *Serratia* is 0.7 micron by 0.9-2.0 micron.

Selection of an appropriate pore size also may depend on the shape and deformability of the target species of interest. For example, when applying a similar force, red blood cells are known to deform more readily than white blood cells. Thus, a sufficient flow force may be applied to selectively allow passage through pores of one species over another (or both) under conditions favoring selective passage of one deformed species only, one undeformed species only, or combinations thereof.

In one embodiment, the filter comprises a filter membrane in the shape of a hollow tube. The filter membrane has a pore size range that is large enough to allow the blood-borne pathogen to pass through and small enough to retain the platelets. In certain embodiments, the filter membrane has a pore size range of 0.02 μm to 10 μm, 0.05 μm to 5 μm, 0.05 μm to 2 μm, 0.05 μm to 1 μm, 0.1 μm to 2 μm, 0.1 μm to 1 μm, 0.2 μm to 5 μm, 0.2 μm to 2 μm, 0.5 μm to 5 μm, or 0.5 μm to 2 μm. In other embodiments, the filter membrane has an average pore size of about 0.2 μm, 0.5 μm, 1 μm, 2 μm, 3 μm or 5 μm.

In certain embodiments, diafiltration membranes with a pore size range of about 0.2-5.0 μm is used to separate platelets (typically about 2.65-2.9 μm in size) from smaller pathogens in the platelet preparation. In one embodiment, the filter membrane has an average pore size of 0.2 μm and is used for the removal of blood-borne viruses. In another embodiment, the filter membrane has an average pore size of 1 μm or 2 μm and is used for the removal of blood-borne viruses and certain small bacteria, such as *Staphylococcus* and *Serratia*. In other embodiments, diafiltration membranes with a pore size range of about 5-12 μm are also used to separate platelets from other cellular blood components and large pathogens in the platelet preparation.

In one embodiment, the present application relates to method for removing blood-borne viruses and bacteria from a platelet preparation prior to transfusion. The method comprises passing the platelet preparation through a tangential flow filtration (TFF) device having a TFF filter with an average pore size of 5 μm, the TFF filter has a retentate side and a permeate side; and collecting a retentate from the TFF device, wherein the retentate comprises filtered platelets to be used for transfusion, wherein a diafiltration solution is added to the retentate and wherein the platelet preparation comprises an platelet activation inhibitor and an anti-coagulant.

In another embodiment, the present application relates to method for removing blood-borne viruses, *Staphylococcus* and *Serratia* from a platelet preparation prior to transfusion. The method comprises passing the platelet preparation through a tangential flow filtration (TFF) device having a TFF filter with an average pore size of 3 μm, the TFF filter has a retentate side and a permeate side; and collecting a retentate from the TFF device, wherein the retentate comprises filtered platelets to be used for transfusion, wherein a diafiltration solution is added to the retentate and wherein the platelet preparation comprises an platelet activation inhibitor and an anti-coagulant.

In another embodiment, the present application relates to method for removing blood-borne viruses from a platelet preparation prior to transfusion. The method comprises passing the platelet preparation through a tangential flow filtration (TFF) device having a TFF filter with an average pore size of 0.2 μm, the TFF filter has a retentate side and a permeate side; and collecting a retentate from the TFF device, wherein the retentate comprises filtered platelets to be used for transfusion, wherein a diafiltration solution is added to the retentate and wherein the platelet preparation comprises an platelet activation inhibitor and an anti-coagulant. In a related embodiment, the blood-borne viruses include HIV and HBV.

In certain embodiments, the filter membranes may be modified to selectively bind target molecules of interest in the platelet composition. In one embodiment, the membrane is chemically modified to provide a greater positive or negative charge. Alternatively, the surface chemistry of these membranes can be modified to specifically bind target molecules of interest, including platelet activation inhibitors, anticoagulants, antibodies and the like. The degree of binding can be designed to provide a specific binding affinity based on biological interactions including, but not limited to, antibody-antigen and ligand-receptor interactions.

The filter membrane can be made of any suitable material. Suitable microfiltration membrane materials, include, but are not limited to, regenerated cellulose, cellulose acetate, polyamide, polyurethane, polypropylene, polysulfone, polyethersulfone, polycarbonate, nylon, polyimide and combinations thereof. In one embodiment, the microfiltration membrane is a hollow fiber membrane made of polysulfone or polyethersulfone.

In certain embodiments, the filter membrane may comprises a nanofiber. Exemplary nanofibers, include, but are not limited to, cellulose nanofibers, biodegradable nanofibers, and carbon nanofibers. Cellulose nanofibers may be obtained from various sources such as flax bast fibers, hemp fibers, kraft pulp, and rutabaga, by chemical treatments followed by innovative mechanical techniques. The nanofibers thus obtained may have diameters between 5 and 60 nm. The ultrastructure of cellulose nanofibers can be investigated by atomic force microscopy and transmission electron microscopy. The cellulose nanofibers also can be characterized in terms of crystallinity. In one embodiment, the membrane filter is a reinforced composite film comprising 90% polyvinyl alcohol and 10% nanofibers. The chemistry of these cellulose fibers can be modified to provide specific binding sites for a given targets, such as platelet activation inhibitors, anticoagulants or antibodies.

Biodegradable polymers, such as poly(glycolic acid) (PGA), poly(L-lactic acid) (PLLA) and poly(lactic-co-glycolic acid) (PLGA), can be dissolved individually in the proper solvents and then subjected to electrospinning process to make nanofibrous scaffolds. Their surfaces can then be chemically modified using oxygen plasma treatment and in situ grafting of hydrophilic acrylic acid (AA). In one embodiment, the biodegradable nanofibrous scaffold has a fiber thickness in the range of 200-800 nm, a pore size in the range of 0.5-2 µm, and porosity in the range of 94-96%.

The ultimate tensile strength of PGA will be typically about 2.5 MPa on average and that of PLGA and PLLA will be typically less than about 2 MPa. The elongation-at-break will be typically about 100-130% for the three nanofibrous scaffolds. When the surface properties of AA-grafted scaffolds are examined, higher ratios of oxygen to carbon, lower contact angles and the presence of carboxylic (—COOH) groups are identified. With the use of plasma treatment and AA grafting, the hydrophilic functional groups can be successfully adapted on the surface of electrospun nanofibrous scaffolds. These surface-modified scaffolds provide the necessary sites for adding ligands specific to the binding of, for example, antibodies, antiplatelet agents, and/or anticoagulants.

In addition, several approaches can be utilized to convert activated carbon into bioreactive fibers. An example is provided to demonstrate the ability of these modified carbon nanofibers to provide carboxylic, hydroxyl and other chemically reactive sites for the binding of any ligand of interest.

Carbon nanofibers (CNF) can be synthesized by chemical vapor deposition (CVD). Amino acids, such as alanine, aspartic acid, glutamic acid and enzymes such as glucose oxidase (GOx) can be adsorbed on CNF. The properties of CNF (hydrophilic or hydrophobic) are characterized by the pH value, the concentration of acidic/basic sites and by naphthalene adsorption. These fibers are readily amenable to crosslinking with ligands of interest, e.g., ligands with the ability to selectively bind to antiplatelet agents, anticoagulants, and the like. Alternatively, or in addition, antibody-binding moieties may be immobilized on any of the filter membranes or porous nanofibers of the present invention to remove antibodies in conjunction with, or in addition to, the diafiltration process.

Pathogens

Pathogens targeted for removal and/or inactivation from platelet composition include any blood borne infectious or pathogenic agents, including viruses, bacteria, fungi, protozoa, and prions. In one embodiment, the pathogens are blood-borne viruses. The pathogens may be targeted for removal by filtration on the basis of size and may be additionally inactivated by treatment with photosensitizers in the presence of light to activate the photosensitizer and inactivate pathogens or cells undergoing nucleic acid replication. Platelets and red blood cells are spared, since they lack nucleic acids. When combining pathogen inactivation with pathogen removal, it is possible to ensure complete removal of all pathogens (by greater than 6 logs) from a platelet composition.

Blood-borne viruses targeted for removal and/or inactivation include cell-free viruses and cell-associated viruses. Some may produce cell-free virus, but can remain strongly cell-associated or latent as well. Exemplary blood-borne viruses include, but are not limited to, human immunodeficiency virus type 1 and type 2 (HIV-1 and HIV-2), human T-cell lymphotropic virus type I and type II (HTLV-I and HTLV-II), hepatitis B virus (HBV), hepatitis C virus (HCV), hepatitis delta virus (HDV), hepatitis E virus (HEV), hepatitis G virus (HGV), parvovirus B19 virus, hepatitis A virus, hepatitis G virus, hepatitis E virus, transfusion transmitted virus (TTV), Epstein-Barr virus, human cytomegalovirus type 1 (HCMV-1), human herpes virus type 6 (HHV-6), human herpes virus type 7 (HHV-7), human herpes virus type 8 (HHV-8), influenza type A viruses, including subtypes H1N1 and H5N1, severe acute respiratory syndrome (SARS) coronavirus, and RNA viruses that causes hemorrhagic fever, such as Arenaviridae (e.g., Lassa fever virus (LFV)), Filoviridae (e.g., Ebola virus (EBOV) and Marburg virus (MBGV)); Bunyaviridae (e.g., Rift Valley fever virus (RVFV) and Crimean-Congo hemorrhagic fever virus (CCHFV)); and Flaviviridae (West Nile virus (WNV), Dengue fever virus (DENY), yellow fever virus (YFV), and (GB virus C (GBV-C), formerly known as Hepatitis G virus (HGV)); and prions, small infectious agents composed of protein in misfolded form, which are typically between about 200 kDa-1,000 kDa in size.

Exemplary blood-borne bacteria include those normally associated with blood or those associated with sepsis. Exemplary blood-borne bacteria, but are not limited to, *Escherichia coli, Staphylococcus aureus, Staphylococcus epidermidis, Bacillus cereus, Eikenella corroders, Enterococcus faecalis, Enterococcus aecium, Listeria monocytogenes, Streptococcus pneumoniae, Streptococcus pyogenes, Streptococcus agalactiae, Escherichia coli, Klebsiella pneumoniae, Haemophilus influenzae, Pseudomonas aeruginosa, Acinetobacter baumannii, Neisseria meningitidis, Neisseria gonorrhoeae, Bacteroides fragilis, Bacillus anthracis, Yersinia pestis, Yersinia enterocolitica, Francisella tularensis, Brucella abortus, Serratia marcescens, Serratia liquelaciens, Pseudomonas fluorescens* and *Deinococcus radiodurans*.

Exemplary blood-borne fungi include *Candida* sp., including *Candida albicans*, and *Aspergillus* sp., including *Aspergillus fumigatus*.

Diafiltration Solution

The diafiltration solution of the present invention is an isosmotic solution. In one embodiment, the diafiltration solution comprises sodium chloride at a final concentration of 0.9% (w/v). In other embodiments, the diafiltration solution is phosphate buffered saline, lactated Ringers solution or lactated Ringers solution with glucose. In yet other embodiments, the diafiltration solution comprises at least one oncotic agent, at least one crystalloid agent, at least one carbohydrate, and/or at least one electrolyte.

The oncotic agent comprises a molecule having a size sufficient to prevent its loss from circulation by traversing fenestrations from the capillary bed into interstitial tissue spaces. Exemplary oncotic agents, include, but are not limited to, dextran (e.g., a low-molecular-weight dextran), dextran derivatives (e.g., carboxymethyl dextran, carboxydextran, cationic dextran, and dextran sulfate), hydroxyethyl starch, hydroxypropyl starch, branched, unsubstituted or substituted starch, gelatin (e.g., modified gelatin), albumin (e.g., human plasma, human serum albumin, heated human plasma protein, and recombinant human serum albumin), PEG, polyvinyl pyrrolidone, carboxymethylcellulose, acacia gum, glucose, a dextrose (e.g., glucose monohydrate), oligosaccharides (e.g., oligosaccharide), a polysaccharide degradation product, an amino acid, and a protein degradation product. Among those, particularly preferable are low-molecular-weight dextran, hydroxyethyl starch, modified gelatin, and recombinant albumin.

In one embodiment, one or more oncotic agent(s) are added to the diafiltration solution in an amount sufficient to provide a viscosity between about 1.1 and 1.3 centipoise.

In another embodiment, the oncotic agent is albumin, preferably at a concentration of about 5% (w/v). In another embodiment, the oncotic agent is a polysaccharide, such as Dextran, in a molecular weight range of 30 to 50 kDa. In yet another embodiment, the oncotic agent is a polysaccharide, such as Dextran, in a molecular weight range of 50 to 70 kDa. High molecular weight dextran solutions are more effective in preventing tissue swelling due to their lower rates of leakage from capillaries. In one embodiment, the concentration of the polysaccharide is sufficient to achieve (when taken together with chloride salts of sodium, calcium and magnesium, organic ion from the organic salt of sodium and hexose sugar discussed above) colloid osmotic pressure approximating that of normal human serum, about 28 mm Hg.

The diafiltration solution may also include one or more crystalloid agents. The crystalloid agent can be any crystalloid capable of achieving an osmolarity greater than 800 mOsm/L, i.e. it makes the diafiltration solution "hypertonic". Examples of suitable crystalloids and their concentrations in the diafiltration solution, include, but are not limited to, 3% w/v NaCl, 7% NaCl, 7.5% NaCl, and 7.5% NaCl in 6% w/v dextran. In one embodiment, the diafiltration solution has an osmolarity of between about 150 and 400 mOsm/L. In another embodiment, the diafiltration solution has an osmolarity between about 300 and 310 mOsm/L.

The diafiltration solution may further include an anti-inflammatory or immunomodulatory agent. Examples of the anti-inflammatory agent shown to inhibit reactive oxygen species including, but not limited to, histidine, albumin, (+) naloxone, prostaglandin $D_2$, molecules of the phenylalkylamine class. Other anti-inflammatory compounds and immunomodulatory drug include interferon; interferon derivatives comprising betaseron, β-interferon; prostane derivatives comprising iloprost, cicaprost; glucocorticoids comprising cortisol, prednisolone, methyl-prednisolone, dexamethasone; immunsuppressives comprising cyclosporine A, methoxsalene, sulfasalazine, azathioprine, methotrexate; lipoxygenase inhibitors comprising zileutone, MK-886, WY-50295, SC-45662, SC-41661A, BI-L-357; leukotriene antagonists; peptide derivatives comprising ACTH and analogs thereof; soluble TNF-receptors; anti-TNF-antibodies; soluble receptors of interleukins or other cytokines; antibodies against receptors of interleukins or other cytokines, T-cell-proteins; and calcipotriols and analogues thereof taken either alone or in combination.

The diafiltration solution also may include one or more electrolytes. The electrolyte to be used in the present invention typically includes various electrolytes to be used for medicinal purposes. Examples of the electrolyte include sodium salts (e.g., sodium chloride, sodium hydrogen carbonate, sodium citrate, sodium lactate, sodium sulfate, sodium dihydrogen phosphate, disodium hydrogen phosphate, sodium acetate, sodium glycerophosphate, sodium carbonate, an amino acid sodium salt, sodium propionate, sodium β-hydroxybutyrate, and sodium gluconate), potassium salts (e.g., potassium chloride, potassium acetate, potassium gluconate, potassium hydrogen carbonate, potassium glycerophosphate, potassium sulfate, potassium lactate, potassium iodide, potassium dihydrogen phosphate, dipotassium hydrogen phosphate, potassium citrate, an amino acid potassium salt, potassium propionate, and potassium β-hydroxybutyrate), calcium salts (e.g., calcium chloride, calcium gluconate, calcium lactate, calcium glycerophosphate, calcium pantothenate, and calcium acetate), magnesium salts (e.g., magnesium chloride, magnesium sulfate, magnesium glycerophosphate, magnesium acetate, magnesium lactate, and an amino acid magnesium salt), ammonium salts (e.g., ammonium chloride), zinc salts (e.g., zinc sulfate, zinc chloride, zinc gluconate, zinc lactate, and zinc acetate), iron salts (e.g., iron sulfate, iron chloride, and iron gluconate), copper salts (e.g., copper sulfate), and manganese salts (for example, manganese sulfate). Among those, particularly preferable are sodium chloride, potassium chloride, magnesium chloride, disodium hydrogen phosphate, dipotassium hydrogen phosphate, potassium dihydrogen phosphate, sodium lactate, sodium acetate, sodium citrate, potassium acetate, potassium glycerophosphate, calcium gluconate, calcium chloride, magnesium sulfate, and zinc sulfate.

Concentration of calcium, sodium, magnesium and potassium ion is typically within the range of normal physiological concentrations of said ions in plasma. In general, the desired concentration of these ions is obtained from the dissolved chloride salts of calcium, sodium and magnesium. The sodium ions may also come from a dissolved organic salt of sodium that is also in solution.

In one embodiment, the sodium ion concentration is in a range from about 70 mM to about 160 mM. In another embodiment, the sodium ion concentration is in a range of about 130 to 150 mM.

In one embodiment, the concentration of calcium ion is in a range of about 0.5 mM to 4.0 mM. In another embodiment, the concentration of calcium ion is in a range of about 2.0 mM to 2.5 mM.

In one embodiment, the concentration of magnesium ion is in a range of about 0 to 10 mM. In another embodiment, the concentration of magnesium ion is in a range of about 0.3 mM to 0.45 mM.

In one embodiment, the concentration of potassium ion is in a subphysiological range between 0-5 mEq/l $K^+$ (0-5 mM), preferably 2-3 mEq/l $K^+$ (2-3 mM). Thus, the diafiltration solution allows for dilution of the potassium ion concentration in a stored platelet composition. As a result, high concentrations of potassium ion and potential cardiac arrhythmias and cardiac insufficiency caused thereby can be more easily controlled.

In one embodiment, the concentration of chloride ion is between about 70 mM to 160 mM. In another embodiment, the concentration of chloride ion is between about 110 mM to 125 mM.

Other sources of ions include sodium salts (e.g., sodium hydrogen carbonate, sodium citrate, sodium lactate, sodium sulfate, sodium dihydrogen phosphate, disodium hydrogen phosphate, sodium acetate, sodium glycerophosphate, sodium carbonate, an amino acid sodium salt, sodium propionate, sodium β-hydroxybutyrate, and sodium gluconate), potassium salts (e.g., potassium acetate, potassium gluconate, potassium hydrogen carbonate, potassium glycerophosphate, potassium sulfate, potassium lactate, potassium iodide, potassium dihydrogen phosphate, dipotassium hydrogen phosphate, potassium citrate, an amino acid potassium salt, potassium propionate, and potassium β-hydroxybutyrate), calcium salts (e.g., calcium gluconate, calcium lactate, calcium glycerophosphate, calcium pantothenate, and calcium acetate), magnesium salts (e.g., magnesium sulfate, magnesium glycerophosphate, magnesium acetate, magnesium lactate, and an amino acid magnesium salt), ammonium salts, zinc salts (e.g., zinc sulfate, zinc chloride, zinc gluconate, zinc lactate, and zinc acetate), iron salts (e.g., iron sulfate, iron chloride, and iron gluconate), copper salts (e.g., copper sulfate), and manganese salts (for example, manganese sulfate). Among those, particularly preferable are sodium chloride, potassium chloride, magnesium chloride, disodium hydrogen phosphate, dipotassium hydrogen phosphate, potassium dihydrogen phosphate, sodium lactate, sodium acetate, sodium citrate, potassium acetate, potassium glycerophosphate, calcium gluconate, calcium chloride, magnesium sulfate, and zinc sulfate.

The diafiltration solution may also contain a carbohydrate or a mixture of carbohydrates. Carbohydrates may be included to provide a nutrient source of intermediate metabolites for platelets. Exemplary carbohydrates, include, but are not limited to, hexoses (e.g., glucose, mannose, galactose, and fructose), pentoses (e.g., aldopentoses, such as ribose and arabinose, and ketopentoses, such as ribulose and xylulose), mannitol, sorbitol, including D- or L-enantiomers thereof, or others known in the art. In one embodiment, the diafiltration solution includes a hexose, such as D-glucose, at concentrations between about 1 mM to 50 mM, preferably between about 2 to 25 mM, still more preferably between about 5 to 20 mM glucose. In another embodiment, the diafiltration solution includes a pentose, such as D-ribose, at concentrations between about 50 nm to 15 μM, preferably between about 100 nm to 5 μM.

Other carbohydrates include various saccharides to be used for medicinal purposes. Examples of the saccharides include xylitol, dextrin, glycerin, sucrose, trehalose, glycerol, maltose, lactose, and erythritol. Amino acids known to prevent apoptosis and to provide nutrition also may be included. Examples of such amino acids include glutamine, glycine, proline and 2-aminopentaenoic acid.

The diafiltration solution may further comprise a biological buffer to maintain the pH of the fluid at the physiological range of pH 7-8.

Examples of biological buffers, include, but are not limited to, N-2-Hydroxyethylpiperazine-N'-2-hydroxypropanesulfonic acid (HEPES), 3-(N-Morpholino) propanesulfonic acid (MOPS), 2-([2-Hydroxy-1,1-bis(hydroxymethyl)ethyl]amino)glyci ethanesulfonic acid (TES), 3-[N-tris(Hydroxymethyl)methylamino]-2-hydroxyethyl]-1-piperazinep ropanesulfonic acid (EPPS), Tris[hydrolymethyl]-aminoethane (THAM), and Tris[Hydroxylmethyl]methyl aminomethane (TRIS).

In one embodiment, the buffering agent is histidine, imidazole, substituted histidine or imidazole compounds retaining the amphoteric site of the imidazole ring, oligopeptides containing histidine, or mixtures thereof. Histidine or imidazole may be used in a concentration range of about 0.0001M to about 0.2M, preferably about 0.0001M to about 0.01M.

In another embodiment, the diafiltration solution uses normal biological components to maintain in vivo biological pH. Briefly, some biological compounds, such as lactate, are capable of being metabolized in vivo and act with other biological components to maintain a biologically appropriate pH in an animal. The biological components are effective in maintaining a biologically appropriate pH even at hypothermic temperatures and at essentially bloodless conditions. Examples of the normal biological components include, but are not limited to carboxylic acids, salt and ester thereof. Carboxylic acids have the general structural formula of RCOOX, where R is an alkyl, alkenyl, or aryl, branched or straight chained, containing 1 to 30 carbons which carbons may be substituted, and X is hydrogen or sodium or other biologically compatible ion substituent which can attach at the oxygen position, or is a short straight or branched chain alkyl containing 1-4 carbons, e.g., —$CH_3$, —$CH_2 CH_3$. Examples of carboxylic acids and carboxylic acid salts, include, but are not limited to, lactate and sodium lactate, citrate and sodium citrate, gluconate and sodium gluconate, pyruvate and sodium pyruvate, succinate and sodium succinate, and acetate and sodium acetate.

In certain embodiments, the diafiltration solution may further comprise one or more antioxidants. Examples of antioxidants, include, but are not limited to, sodium hydrogen sulfite, sodium sulfite, sodium pyrosulfite (e.g., sodium metabisulfite), rongalite ($CH_2OHSO_2Na$), ascorbic acid, sodium ascorbate, erythorbic acid, sodium erythorbate, cysteine, cysteine hydrochloride, homocysteine, glutathione, thioglycerol, α-thioglycerin, sodium edetate, citric acid, isopropyl citrate, potassium dichloroisocyanurate, sodium thioglycolate, sodium pyrosulfite 1,3-butylene glycol, disodium calcium ethylenediaminetetraacetate, disodium ethylenediaminetetraacetate, an amino acid sulfite (e.g, L-lysine sulfite), butylhydroxyanisole (BHA), butylhydroxytoluene (BHT), propyl gallate, ascorbyl palmitate, vitamin E and derivatives thereof (e.g., dl-α-tocopherol, tocopherol acetate, natural vitamin E, d-δ-tocopherol, mixed tocopherol, and trolox), guaiac, nordihydroguaiaretic acid (NDGA), L-ascorbate stearate esters, soybean lecithin, palmitic acid ascorbic acid, benzotriazol, and pentaerythrityl-tetrakis[3-(3,5-di-t-butyl-4-hydroxyphenyl)propionate]2-mercaptobenzimidazole.

Among those, preferable are sodium hydrogen sulfite, sodium sulfite, ascorbic acid, homocysteine, dl-α-tocopherol, tocopherol acetate, glutathione, and trolox.

In addition to the components discussed above, the diafiltration solution may further comprise other additives that, include, but are not limited to, antibiotics, such as penicillin, cloxacillin, dicloxacillin, cephalosporin, erythromycin, amoxicillin-clavulanate, ampicillin, tetracycline, trimethoprim-sulfamethoxazole, chloramphenicol, ciprofloxacin, aminoglycoside (e.g., tobramycin and gentamicin), streptomycin, sulfa drugs, kanamycin, neomycin, land monobactams; anti-viral agents, such as amantadine hydrochloride, rimantadin, acyclovir, famciclovir, foscarnet, ganciclovir sodium, idoxuridine, ribavirin, sorivudine, trifluridine, valacyclovir, vangancyclovir, pencyclovir, vidarabin, didanosine, stavudine, zalcitabine, zidovudine, interferon alpha, and edoxudine; anti-fungal agents such as terbinafine hydrochloride, nystatin, amphotericin B, griseofulvin, ketoconazole, miconazole nitrate, flucytosine, fluconazole, itraconazole, clotrimazole, benzoic acid, salicylic acid, voriconazole, caspofungin, and selenium sulfide; vitamins, amino acids, vessel expanders such as alcohols and polyalcohols, surfactants, antibodies against harmful cytokines such as tumor necrosis factor (TNF) or interleukins, and mediators of vascular potency, such as prostaglandins, leukotrienes, and platelet activating factors.

Exemplary plasma free solutions for use in the diafiltration solution of the present invention, include, but are not limited to, InterSol® (Fenwal Inc., Lake Zurich, Ill.), T-Sol, PAS II, PAS IIIM, PAS27 (Baxter). In one embodiment, the diafiltration solution is a commercially available platelet storage solution (T-Sol) with no plasma. In another embodiment, the diafiltration solution is InterSol® with no plasma. In another embodiment, the diafiltration solution is normal saline (0.9% NaCl) or Ringer's lactate, or D5NS (5% dextrose in normal saline).

Diafiltration Process

Filtration is a pressure driven separation process that ses filters comprising membranes, in this case, to separate components in a liquid solution or suspension based on their size differences. Filtration can be broken down into two operational modes: normal flow filtration (NFF) and tangential flow filtration (TFF). In NFF, fluid is converted directly toward the membrane under an applied pressure. Particulates that are too large to pass through the pores of the membrane accumulate at the membrane surface or in the depth of the filtration media, while smaller molecules pass through to the downstream side. This process is also known as dead-end filtration.

In TFF, the fluid is pumped tangentially along the surface of the membrane. An applied pressure serves to force a portion of the fluid through the membrane to the permeate side. As in NFF, particulates and macromolecules that are too large to pass through the membrane pores are retained on the upstream side. However, in this case the retained components do not build up at the surface of the membrane. Instead, they are swept along by the tangential flow. TFF is also commonly called cross-flow filtration. However, the term "tangential" is descriptive of the direction of fluid flow relative to the membrane.

Diafiltration is a TFF method of "washing" or removing permeable molecules (impurities, salts, solvents, proteins, etc.) from a solution. Because it is a significantly faster and scalable method, diafiltration frequently replaces membrane tube dialysis. The success of diafiltration is largely determined by selection of an appropriate membrane based on the size(s) of the target species for retention or removal and careful attention to flow rates. The membrane pores must be large enough to allow designated permeable species to pass through the membrane into a permeate fraction, but small enough to retain other designated larger species, such as cellular components, in the retentate fraction. A desired target species may fractionate in the permeate or retentate fraction.

FIG. 1 shows an exemplary continuous diafiltration system 100 in which the diafiltration buffer is automatically added to the process reservoir by vacuum suction. The system includes a pump 101, a sample reservoir 103, a diafiltration solution reservoir 105, a filter 107, a permeate reservoir 109, as well as pressure measurement device and flow easurement device (not shown). The pump 101 circulates the platelet composition in the sample reservoir 103, through the filter 107 and back to the sample reservoir 103 at a controlled flow and shear rate. Pressure measurements are acquired in this re-circulation loop to control and record the driving force through the filter 107. Careful measurement of the permeate flow rate enables accurate process scale up and process optimization. Diafiltration is a process in which clean diafiltration buffer is added to the diafiltration solution reservoir 105 in this circulation loop with the goal of "washing out" one or more permeable species into the permeate reservoir 109. The process of continuous diafiltration is when diafiltration solution is added to the process material in the sample reservoir 103 at the same rate permeate is exiting the filter 107. The filter 107, tubing, bottles, and air-tight vacuum provide a simple means for performing a continuous diafiltration, which is self-regulating and constant flow process.

To begin the diafiltration in an airtight vacuum system, a buffer addition tube is submerged into a bottle of diafiltration solution as shown in FIG. 1. As permeate flows out of the system, the vacuum in the sealed process reservoir pulls the diafiltration solution into it at a flow rate equal to the process flux (permeate flow rate per unit area). When the target volume of diafiltration solution has been collected in the permeate reservoir 109, the process is stopped simply by stopping the permeate flow and breaking the vacuum seal (e.g., open a vent valve) on the sample reservoir 103.

In one embodiment, an extraction liquid is circulated through the permeate side of the filter in a counter current manner to facilitate the filtration process. In a related embodiment, the extraction fluid comprises 0.9% w/v sodium chloride. When airtight systems are not possible, particularly for pilot and manufacturing scale processes, diafiltration solution addition can be controlled to match the permeate flow rate through the use of a single- or double-headed secondary pump adding diafiltration solution into the sample reservoir 103.

FIG. 1 is representative of a continuous diafiltration system using a hollow fiber module. The system and methods of the present invention can be modified as a non-continuous TFF system using other filters or filter membrane modules described herein using methods known to those of skill in the art.

Typically, a filter with a predetermined pore size is selected so that species of interest is retained in the retentate. Depending on the sizes of blood components and the requirements for separation, a plurality of filters differing in pore size from another may be used in a sequential manner as described above.

The flow rate may be optimized for effective separation of plasma and/or cellular components from platelets so as to maintain a shear force that does not adversely affect the functional activity or structural integrity of platelets. For example, the shear force should not cause activation of platelets. In some embodiments, a platelet composition of about $3 \times 10^{11}$ cells is passed through a hollow fiber membrane filter having a total membrane filter surface area of 2500 cm$^3$, wherein the flow rate is between 20 ml/min to 3500 ml/min, 100 ml/min to 650 ml/min, or 250 to 500 ml/min. Representative flow rates also may be expressed in relation to both total membrane filter surface area and total number of diafiltered cells of interest, wherein 1 Flow Rate Quotient (FRQ) is equal to 1 ml/min of diafiltration fluid flow rate per otal membrane filter surface area (cm$^3$)/total number of diafiltered cells of interest. Thus, exemplary flow rates may range between about 0.01 to 1.5 FRQ, between about 0.05 to 0.25 FRQ, or between about 0.1 to 0.2 FRQ.

When used with an appropriate filter or filter membrane(s), these flow rate values can provide acceptable shear forces from about 2000-s to about 4000-s. In certain embodiments, the plasma removal process is carried out with 5, 8, 10, 12, 15 or 20 volume exchanges of diafiltration solution. In one embodiment, the plasma removal process is carried out with 10-12 volume exchanges of diafiltration solution. In another embodiment, the plasma removal process is carried out with 15 volume exchange of diafiltration solution. The diafiltration process can be performed as a discontinuous volume exchange, a constant volume exchange, or both. In a discontinuous volume exchange, the fluid containing the blood components is alternatively diluted and concentrated. In a constant volume exchange, the volume of the fluid containing the blood components is maintained constant. In both cases, one volume exchange of diafiltration solution is defined as the addition of diafiltration solution at a volume that equals to the original volume of the blood component composition. Both methods can be readily combined to reduce the total volume of exchange fluid required. Such volume exchanges can result in up to a 6 log removal of most non-cellular blood components (>99.9999%), as well as exogenously added agents (e.g., antiplatelet agents and anticoagulants).

In one embodiment, the filter comprises a hollow fiber membrane with a pore size of 0.2-2.0 µm, 0.2-1.0 µm or 0.5-1.0 µm. For the exchange of one unit of platelets (300 to 400 ml), a preferred surface area of the filtration module may be about 2500 cm$^2$, which, along with a flow rate of 370 ml/min, can allow for the removal (4 to 6 log) of plasma and antiplatelet/anticoagulant agents contained in a unit of platelets in about 15 minutes. This corresponds to about 0.148 FRQs.

Pumps, pressure monitors, and pressure transducers can provide a wide range of flow rates, and allow for continuous monitoring of inlet, retentate, permeate and transmembrane pressures. Exemplary TFF filters, pumps, pressure monitors and transducers, tubing, reservoir vessels, hardware, software, and other TFF filters & systems can be obtained from Spectrum Laboratories (Rancho Dominguez, Calif.), Millipore Corporation (Billerica, Mass.), and Pall Corporation (Port Washington, N.Y.).

In certain embodiments, the method comprises a pre-filtration step to remove the cellular blood components, including cell-associated pathogens, from the platelet preparation. This step may be performed with non-tangential flow filtration or TFF with a filter having a pore size that allows the platelets but not the other cellular blood components to pass through. The filtered platelets are then subjected to the TFF to remove cell-free pathogens. In one embodiment, the platelet preparation is subjected to a first TFF process with a large pore filter (e.g., a pore size of 5 µm, 7.5 µm, 10 µm, 12 µm or larger) to remove cellular blood components, large pathogens and cell-associated pathogens. The permeate of the first TFF process, which contains platelets, is collected and subjected to a second TFF process to remove small cell-free pathogens with a small pore filter (e.g., a pore size of 5 µm, 2.5 µm, 1 µm or smaller).

Alternatively, the platelet preparation may be subjected to a first TFF process with a small pore filter (e.g., a pore size of 5 µm, 2.5 µm, 1 µm or smaller) to remove cell-free pathogens. The retentate, which contains platelets, is then subjected to a second TFF process with a large pore filter (e.g., a pore size of 5 µm, 7.5 µm, 10 µm, 12 µm or larger) to remove cellular blood components, large pathogens and cell-associated pathogen. The permeate, which contains platelets, is collected for transfusion or storage.

Pharmaceutical Platelet Compositions

The method of the present invention can be used to prepare a platelet composition. The transfusion grade platelet composition according to the present invention is a platelet composition prepared by the pathogen removal method of the present invention. The transfusion grade platelet composition of the present invention is preferably free of detectable pathogens. In certain embodiments, the transfusion grade platelet composition of the present invention exhibits an at least 4-log, 5-log, 6-log or 7-log reduction in pathogens compared to the platelet preparation prior to the pathogen removal.

In other embodiments, the transfusion grade platelet composition exhibits substantially reduced levels of antibodies, pathogens, and other undesired agents as described above. Preferably the transfusion grade platelet solution will exhibit a reduction in antibodies of at least 95%, 99%, 99.9%, or 99.99%, or exhibit an at least 4-log, 5-log, 6-log or 7-log reduction in antibodies compared to the platelet preparation prior to the pathogen removal process. In addition, the transfusion grade platelet composition preferably exhibits a reduction in blood-borne viruses of at least 95%, 99%, 99.9%, or 99.99%, or exhibit an at least 4-log, 5-log, 6-log or 7-log reduction in blood-borne viruses compared to the platelet preparation prior to the pathogen removal process.

The diafiltration process can be performed one more times prior to transfusion of the platelets. In one embodiment, the diafiltration process is performed following recovery of the platelet composition. The recovered platelets in the retentate can then be stored before use. In another embodiment, the diafiltration process is performed immediately prior to use. In another embodiment, the diafiltration process is performed twice; once prior to storage and a second time prior to use in transfusion.

Processed platelet compositions. including platelet storage compositions, may be stored in a range of temperatures between about −80° C. to about 42° C. As used herein, the term "room temperature" or "ambient temperature" refers to a temperature in the range of 12° C. to 30° C.; the term "body temperature" refers to a temperature in the range of 35° C. to 42° C.; the term "refrigeration temperature" refers to a temperature in the range of 0° C. to 12° C.; and the term "freezing temperature" refers to a temperature below 0° C. The term "cold storage" or "storage at low temperature" refers to storage at −20° C. to 12° C., preferably 2° C. to 12° C., more preferably 4° C. to 8° C.

Platelets may be stored for a desired period of time. In certain embodiments, the desired period of time is one, two, three or four weeks at room temperature or at 4° C. to 8° C. In some cases, it may be necessary to supplement the cell storage compositions with a plasma portion prior to transfusion. In this case, the plasma portion may comprise no more than: 30% of the transfusion composition, 25%, 20%, 15%, 10%, 5% or 1% of the transfusion composition. However, where such supplementation is necessary, antibodies are preferably removed from the plasma portion prior to its addition to the cellular diafiltration solution (and transfusion) as described above.

The present invention is further illustrated by the following examples which should not be construed as limiting. The contents of all references, patents and published patent applications cited throughout this application, as well as the Figures and Tables are incorporated herein by reference.

Example 1

Removal of Integrilin using Diafiltration

A standard UV absorbance curve at 214 nm with Integrilin concentrations ranging from 3 to 50 µg/ml was established based on the following measurements:

| Integrilin Concentration | O.D 214 |
| --- | --- |
| 50 µg/ml | 0.710 |
| 25 µg/ml | 0.532 |
| 12.5 µg/ml | 0.299 |
| 6.25 µg/ml | 0.126 |
| 3.125 µg/ml | 0.015 |

A test fluid containing 50 µg/ml Integrilin was circulated through a hollow fiber filter (Spectrum Laboratories X20S-300-02S) at a circulation rate of 100 ml/min. Briefly, the test fluid was placed in an air tight container with a starting OD214 of 0.710. As the test fluid circulated through the hollow fiber filter, the retentate volume decreased. The lost fluid volume was replaced with fresh fluid from a second container. After about a 10 minute circulation and a six volume exchange, the OD214 of the test fluid was less than 0.01.

Example 2

Removal of Inhibitors from Platelet Concentrate

Figure 2:
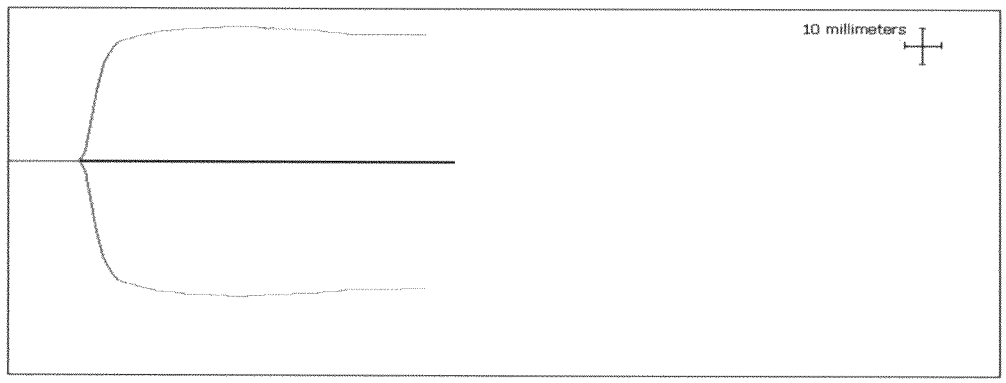
FIG. 2 is a thromboelastogram (TEG) of platelets with inhibitors before (black) and after plasma filtration (green).
Figure 3:
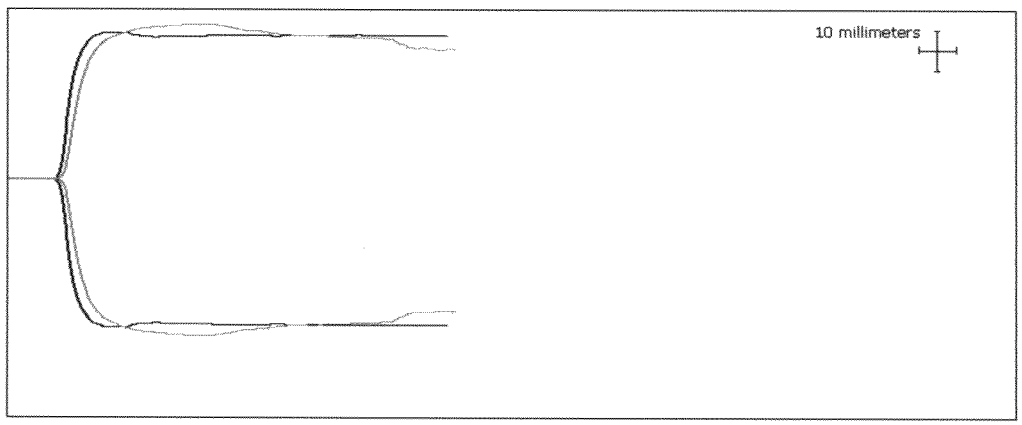
FIG. 3 is a TEG of platelets with saline before (black) and after plasma filtration (green).
Figure 4:
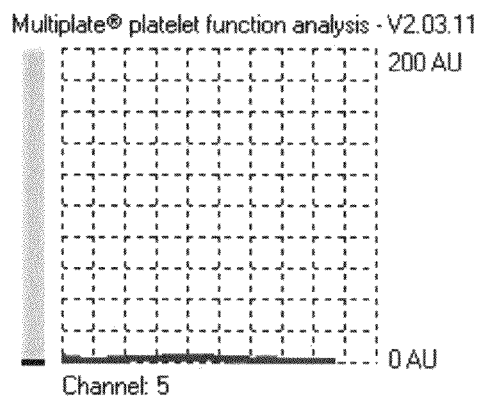
FIG. 4 is a diagram showing the platelet response to thrombin related activated peptide (TRAP) in the presence of the inhibitors.
Figure 5:
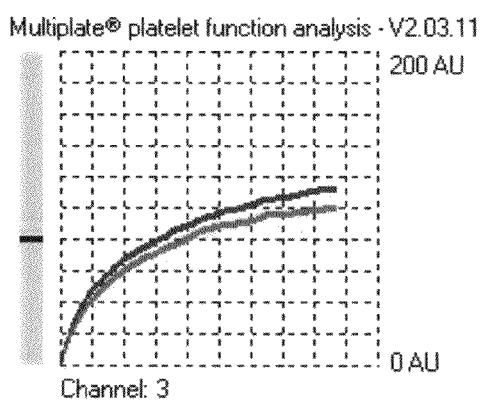
FIG. 5 is a diagram showing the platelet response to TRAP after the removal of the inhibitors.
Figure 6:
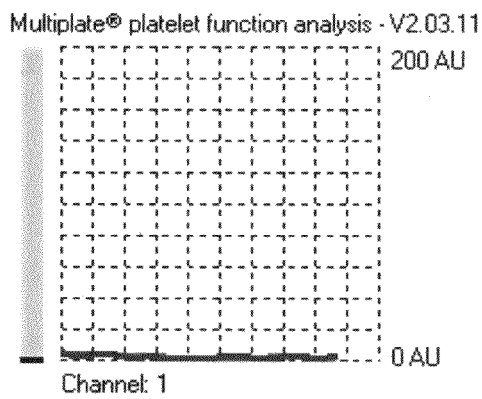
FIG. 6 is a diagram showing the platelet response to collagen in the presence of the inhibitors.
Figure 7:
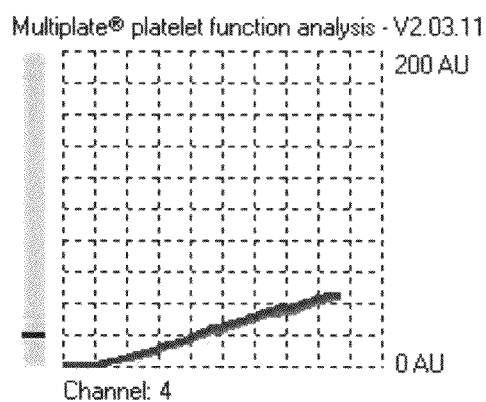
FIG. 7 is a diagram showing the platelet response to collagen after the diafiltration.

In one experiment, platelet concentrates obtained by the buffy coat method were used for the study. Integrilin (Eptifibatide), a GPIIb/IIIa inhibitor, and Argabotran, a synthetic thrombin inhibitor, were added to platelet units at three times the therapeutic concentrations (i.e., 48 micrograms of Integrilin and 2.4 mg of Argatroban in 350 ml of platelets). Removal of the inhibitors was initiated by diafiltration. 15 ml of the platelet concentrate was diafiltered against 60 ml of a solution containing 20% fresh frozen plasma in a commercially used platelet storage solution (T-Sol). The samples were stored overnight and platelet functionality was measured on Day 2, by Thromboelastography (TEG) and using standard agonists such as TRAP and collagen. FIG. 2 shows the TEG scan of the test sample before (black line) and after diafiltration (green line). FIG. 3 shows the TEG scan of a control sample (platelets with saline) before (black line) and after diafiltration (green line). The result in FIG. 3 suggests that most inhibitors had been removed by diafiltration. FIG. 4 shows the response to TRAP in the presence of the inhibitors. FIG. 5 shows the response to TRAP after the removal of the inhibitors. FIG. 6 shows the response to collagen in the presence of the inhibitors and finally FIG. 7 shows the response to Collagen after the diafiltration.

In another experiment, Integrilin and Argabotran were added to platelet units at three times the therapeutic loading concentrations (i.e., 48 micrograms for Integrilin and 2.4 mg for Argatroban in 350 ml of platelets). Prior to the addition of the inhibitors, baseline data of platelet functionality was obtained. These baseline data included thromboelastography, which assesses overall platelet function and clot strength, as well as the TRAP test and the collagen test, which are additional markers of platelet functionality.

The diafiltration was conducted in 40 ml aliquots using an airtight 50 ml conical flask, a polysulfone hollow fiber cross flow module with a surface area of 240 cm$^2$. A sequential exchange with increasing volumes of standard platelet additive solution (InterSol®), indicated that a 15 volume exchange provided optimum results with the inhibitors. The pore size of the hollow fiber membrane selected was 0.05 micron. The pore size can range from 3000 daltons molecular weight cut off to 0.5 micron or larger. The 15 volume exchange can be conducted with any currently available additive solution used for storing platelets.

Following the 15 volume exchange, homologous fresh frozen plasma was added to the platelets to achieve a plasma concentration of 25% (v/v). This is required because the plasma provides the soluble components of coagulation, thereby permitting the functionality tests performed.

The recirculation rate of the platelets (in InterSol® containing 30% plasma) was set at 370 ml/minute. This was calculated to create a shear force of approximately 4000-s. This shear force has been shown not to activate platelets.

The inlet pressure over three experiments was 8.13 psi, the retentate pressure was 6.15 psi. The pressure differential was 2 psi. The permeate pressure was essentially 0 and the transmembrane pressure was 7.15 psi. These pressures remained very constant throughout the exchange, indicating no fouling of the membrane. The permeate flow rate was around 26 ml/minute.

When Argatroban is present, it completely blocks the activation of platelets and hence on the thromboelastogram, one sees a straight line. FIG. 7 shows the thromboelastograms of platelets without the inhibitors. The R value, i.e., the time it takes before the clot starts to form, as indicated by the splitting of the line, averaged 10.7 minutes. Following the 15 volume exchange, the average R value was 10.75. In a total of 4 experiments conducted, the R value after 15 volume exchange was equal to or less than the baseline R value. Based on the thromboelastogram, at least a 99.99% removal of inhibitors was achieved.

The maximum amplitude, MA, was unchanged from baseline, when the slight dilution of the platelets during the 15 volume exchange is taken into consideration. This parameter reflects the removal of Integrilin.

Figure 8:
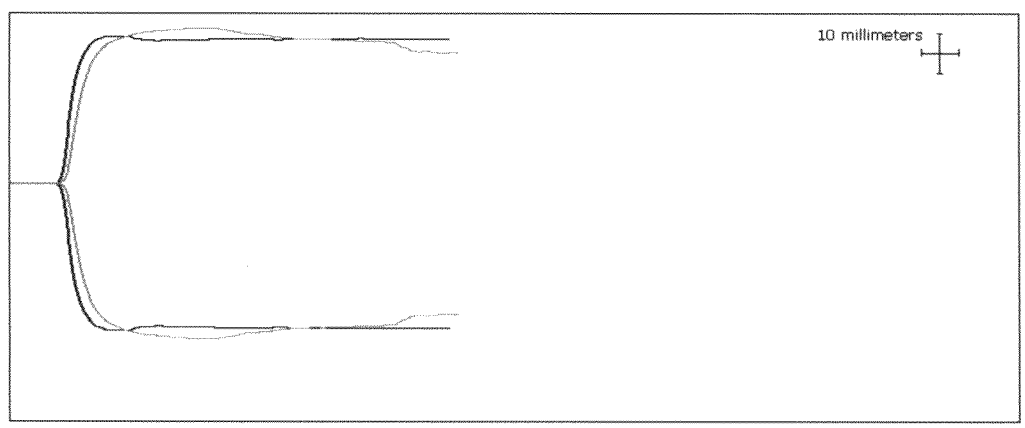
FIG. 8 is a TEG showing (black line) platelets without inhibitors and platelets after the antiplatelet agents had been removed with 15 volume exchange (green line).
Figure 9:
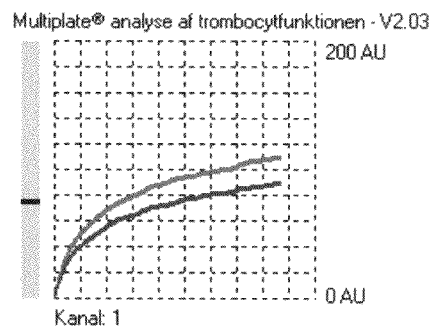
FIG. 9 is a diagram showing the platelet response to TRAP in the absence of the inhibitors.

FIG. 8 shows the results of the TRAP assay run on the platelets prior to the addition of the inhibitors. The area under the curve is expressed as standardized units. The control had a value of 67. The same assay run on the platelets after 15 volume exchange with InterSol® was 68 (FIG. 9). This assay is more sensitive to the presence of Integrilin. It therefore indicates essentially complete removal of this inhibitor.

Figure 10:
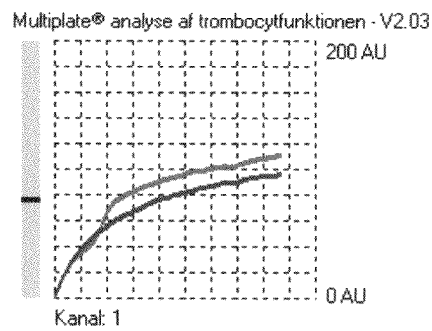
FIG. 10 is a diagram showing the platelet response to TRAP after the removal of inhibitor by 15 volume exchange with InterSol®.
Figure 11:
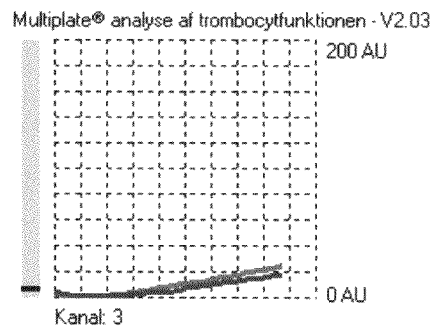
FIG. 11 is a diagram showing the platelet response to collagen in the absence of the inhibitors.

The functionally of the platelets was also tested using collagen as the activator. The baseline value for the platelets was 6 (FIG. 10). The value obtained for the platelets following the removal of the inhibitors with 15 volume exchange with InterSol® was also 6 (FIG. 11).

The experiment described above is a method by which complete replacement of plasma in platelet concentrates, whether collected by apheresis, buffy coat or any other method, can be readily accomplished.

Example 3

Removal of Plasma from Platelet Concentrate

Plasma was removed from a platelet concentrate by diafiltration using a tangential flow filter. A 40 mL aliquot of platelets obtained by apheresis was processed though a tangential flow filter with a combination of discontinuous and constant volume exchange. Discontinuous diafiltration was performed by a four volume (160 ml) exchange. This was followed by a constant volume exchange with the chamber sealed, which allows for the loss to the permeate line to be replaced, drop for drop, by addition to the process reservoir of fresh diafiltration buffer in the buffer reservoir as described above.

Figure 12:
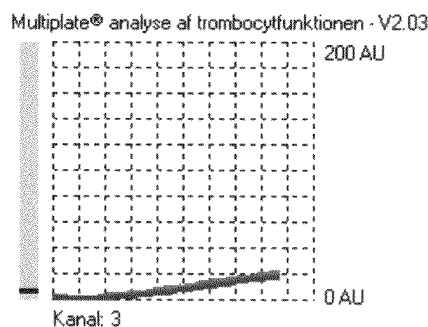
FIG. 12 is a diagram showing the platelet response to collagen after the removal of inhibitor by 15 volume exchange with InterSol®.

Protein levels were determined from human platelet samples treated by diafiltration. Human platelet solutions were spiked either with 0.1 µg/mL Tirofiban and 0.2 µg/mL Eptitibatide (samples 1-7) or 0.1 µg/mL Tirofiban and 8 µg/mL Argatroban (samples 8-10) (FIG. 12).

Figure 13:
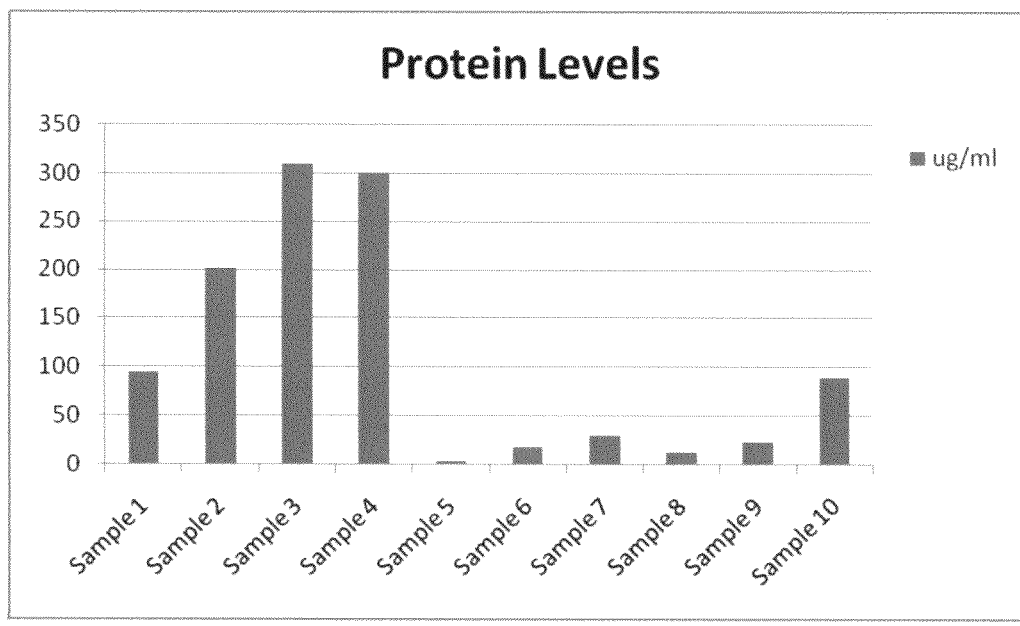
FIG. 13 is a diagram showing protein levels reflecting removal of plasma components following diafiltration.

Protein levels were determined via BCA method after centrifugation to remove platelets. Protein levels in 10 samples treated via diafiltration and 2 control samples (non-diafiltered) were determined using a Pierce BCA (bicinchoninic acid) Protein Assay (Thermo Fisher Pierce; Rockford, Ill.) according to manufacturer's instructions (FIG. 13). A bovine serum albumin (BSA) standard supplied by the kit manufacturer was used to prepare a standard curve over a protein concentration range of 20-2,000 µg/mL. All samples were run neat, with exception of the 2 non-diafiltered control samples which were diluted 1:100 in 0.5% sterile saline.

The results from this analysis showed that modifications made to the diafiltration protocol in day two resulted in substantially less protein (1.1-13.0% of the averaged levels of samples 1-4) in the samples after diafiltration. Relative to samples prior to diafiltration (the average protein concentration of samples 1-10 [Protein]$^{AVE}$=28,750 µg/mL), samples 1-4 had an average of 99.21% of total protein depleted, whereas samples 5-10 averaged 99.90% of total protein depleted. Sample 5 exhibited the most effective removal of protein, greater than 99.99% protein depletion.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A method for removing pathogens from a platelet preparation prior to transfusion, comprising:
   Passing said platelet preparation through a first tangential flow filtration (TFF) device having a TFF filter with an average pore size in the range of 0.2 µm to 5 µm, said TFF filter has a retentate side and a permeate side, wherein said platelet preparation comprises a platelet activation inhibitor and an anticoagulant, said platelet activation inhibitor comprises a short to ultra-short GPIIb/IIIA inhibitor and said anticoagulant comprises a short to ultra-short acting factor Xa inhibitor; and
   Collecting retentate from said first TFF device, wherein said retentate comprises filtered platelets to be used for transfusion,
   Wherein a diafiltration solution is added to said retentate.

2. The method of claim 1, further comprising flowing an extraction fluid on the permeate side of said TFF filter in a counter flow direction relative to the flow of the platelet preparation.

3. The method of claim 1 wherein said TFF filter comprises hollow fibers.

4. The method of claim 3, wherein said hollow fibers have an inner diameter of at least 0.5 mm.

5. The method of claim 1, wherein said TFF filter comprises cellulose nanofibers, biodegradable nanofibers, or a reinforced composite film comprising about 90% polyvinyl alcohol and about 10% nanofiber.

6. The method of claim 1, wherein said TFF filter comprises a material selected from the group consisting of regenerated cellulose, cellulose acetate, polyamide, polysulfone, polyethersulfone, and combinations thereof.

7. The method of claim 1, wherein said TFF titter comprises a filter membrane having a thickness between about 200 to about 800 nm, a pore size between about 2 µm to about 30 µm, and a porosity between about 94% to about 96%.

8. The method of claim 1, wherein said platelet preparation further comprises a photosensitizer and wherein said method further comprises the step of illuminating said platelet preparation, prior to said passing step, with light under conditions sufficient to activate the photosensitizer and inactivate one or more pathogens in said platelet preparation.

9. The method of claim 8, wherein said photosensitizer is selected from the group consisting of riboflavin, psoralen and methylene blue.

10. The method of claim 1, wherein said platelet preparation further comprises an oxygen carrier.

11. The method of claim 10, wherein said oxygen carrier is a hemoglobin based oxygen carrier.

12. The method of claim 1, further comprising the step of passing said retentate through a second TFF device having a TFF filter with an average pore size in the range of 5 µm to 12 µm; and
   collecting a permeate from said second TFF device,
   wherein said permeate contains platelets to be used for transfusion.

13. The method of claim 1, further comprising the step of prior to said passing step, flowing said platelet preparation through a pre-filtration TFF device having a TFF filter with an average pore size in the range of 5 µm to 12 µm; collecting a permeate from said pre-filtration TFF device; and
   passing said permeate through said first TFF device.

14. The method of claim 1, wherein said pathogens comprise bacteria or blood-borne viruses, and wherein said TFF filter has an average pore size of about 5 µm.

15. The method of claim 1, wherein said pathogens comprise blood-borne viruses, *Staphylococcus* or *Serratia*, and wherein said TFF filter has an average pore size of about 3 µm.

16. The method of claim 1, wherein said pathogen is blood-borne virus, and wherein said TFF filter has an average pore size of about 0.2 µm.

17. The method of claim 16, wherein said blood-borne virus is human immunodeficiency virus (HIV) and/or hepatitis B virus (HBV).

18. A method for preparing isolated platelets for storage, comprising:
   Passing said isolated platelets through a first tangential flow filtration (TFF) device having a TFF filter with an average pore size in the range of 0.2 µm to 5 µm, said TFF filter has a retentate side and a permeate side;
   Collecting a retentate from said first TFF device, wherein said retentate comprises filtered platelets; and
   Adding to said retentate an effective amount of a platelet activation inhibitor and an effective amount of an anticoagulant, said platelet activation inhibitor comprises a short to ultra-short GPIIb/IIIA inhibitor and said anticoagulant comprises a short to ultra-short acting factor Xa inhibitor.

19. The method of claim 18, further comprising the steps of:
   adding to said retentate an effective amount of a photosensitizer; and
   illuminating said retentate with light under conditions sufficient to activate the photosensitizer and inactivate one or more pathogens in said retentate.

20. The method of claim 19, wherein said photosensitizer is selected from the group consisting of riboflavin, psoralen and methylene blue.

21. The method of claim 18 further comprising the steps of:
   adding to said retentate an effective amount of an oxygen carrier.

22. The method of claim 18, further comprising the step of prior to said passing step, flowing said isolated platelets through a pre-filtration TFF device having a TFF filter with an average pore size in the range of 5 µm to 12 µm;
   collecting a permeate from said pre-filtration TFF device; and
   instead of passing said isolated platelets through a first TFF device, passing said permeate through said first TFF device.

23. The method of claim 18, further comprising the step of passing said retentate through a second TFF device having a TFF filter with an average pore size in the range of 5 µm to 12 µm;
   collecting a permeate from said second TFF device; and
   instead of adding to said retentate an effective amount of a platelet activation inhibitor and an effective amount of an anti-coagulant, adding to said permeate from said second TFF device an effective amount of a platelet activation inhibitor and an effective amount of an anticoagulant.

24. A method for removing blood-borne virus from a platelet preparation prior to transfusion, comprising:
   Passing said isolated platelets through a first tangential flow filtration (TFF) device having a TFF filter with an average pore size in the range of 0.2 µm to 5 µm, said TFF filter has a retentate side and a permeate side, wherein said platelet preparation comprises a platelet activation inhibitor and an anticoagulant, said platelet activation inhibitor comprises a short to ultra-short GPIIb/IIIA inhibitor and said anticoagulant comprises a short to ultra-short acting factor Xa inhibitor;

Collecting retentate from said TFF device, wherein said retentate comprises filtered platelets to be used for transfusion, Wherein a diafiltration solution is added to said retentate.

25. The method of claim 24, wherein said blood-borne virus comprises human immunodeficiency virus (HIV) or hepatitis B virus (HBV).

* * * * *